United States Patent
Radl et al.

(10) Patent No.: US 12,220,520 B2
(45) Date of Patent: Feb. 11, 2025

(54) LEAKAGE RESISTANT EXTERNAL FEMALE CATHETER SYSTEM AND METHOD OF USE

(71) Applicant: Boehringer Technologies, LP, Phoenixville, PA (US)

(72) Inventors: Christopher L. Radl, Malvern, PA (US); Michael Reed Vennel, Phoenixville, PA (US)

(73) Assignee: Boehringer Technologies, LP, Phoenixville, PA (US)

( * ) Notice: Subject to any disclaimer, the term of this patent is extended or adjusted under 35 U.S.C. 154(b) by 410 days.

(21) Appl. No.: 17/750,720

(22) Filed: May 23, 2022

(65) Prior Publication Data

US 2022/0280711 A1  Sep. 8, 2022

Related U.S. Application Data

(63) Continuation-in-part of application No. 16/996,214, filed on Aug. 18, 2020, now Pat. No. 11,395,871.
(Continued)

(51) Int. Cl.
*A61M 1/00* (2006.01)
*A61F 5/455* (2006.01)

(52) U.S. Cl.
CPC ........... *A61M 1/7415* (2021.05); *A61F 5/455* (2013.01); *A61M 1/742* (2021.05); *A61M 1/743* (2021.05); *A61M 2202/0496* (2013.01)

(58) Field of Classification Search
CPC .... A61M 1/7415; A61M 1/742; A61M 1/743; A61M 2202/0496; A61M 27/00; A61M 1/87; A61M 2210/1092; A61M 1/741; A61M 1/00; A61M 1/84; A61M 1/71; A61F 5/455; A61F 2013/4506; A61F 5/453;
(Continued)

(56) References Cited

U.S. PATENT DOCUMENTS 4,465,481 A   8/1984 Blake
4,610,675 A   9/1986 Triunfol
(Continued)

FOREIGN PATENT DOCUMENTS

WO   2014085099 A1   6/2014

OTHER PUBLICATIONS https://www.crbard.com/Medical/en-US/Products/PUREWICK-Female-External-Catheter, undated, 1 page.
(Continued)

*Primary Examiner* — Philip R Wiest
*Assistant Examiner* — Brandon W. Levy
(74) *Attorney, Agent, or Firm* — Caesar Rivise, PC

(57) ABSTRACT

A system and method for automatically removing by suction urine voided by a female. The system includes an external catheter. The external catheter includes a suction tube having a portion enclosed in a hydrophilic sponge cover. The suction tube is arranged to be coupled to suction of a desired value. The cover is arranged to be disposed externally at the female's urethra opening to receive urine voided by the female, whereupon the suction draws the urine through the cover into the suction tube. The external catheter is arranged to be connected to a receptacle for collecting the urine received by the external catheter. Various embodiments of the suction tube and the cover are disclosed.

4 Claims, 13 Drawing Sheets

Related U.S. Application Data

(60) Provisional application No. 62/924,326, filed on Oct. 22, 2019.

(58) Field of Classification Search
CPC ...... A61F 13/05; A61F 5/4553; A61F 5/4554; A61B 17/3415
See application file for complete search history.

(56) References Cited

U.S. PATENT DOCUMENTS

| | | | |
|---|---|---|---|
| 4,747,166 A | 5/1988 | Kuntz | |
| 5,073,172 A | 12/1991 | Fell | |
| 5,678,564 A * | 10/1997 | Lawrence | A61F 5/455 |
| | | | 600/573 |
| 5,894,608 A | 4/1999 | Birbara | |
| 6,024,120 A | 2/2000 | Yam et al. | |
| 6,849,065 B2 | 2/2005 | Schmidt et al. | |
| 7,018,366 B2 | 3/2006 | Easter | |
| 7,220,250 B2 | 5/2007 | Suzuki et al. | |
| 8,287,508 B1 | 10/2012 | Sanchez | |
| 10,646,625 B2 | 5/2020 | Radl et al. | |
| 2004/0006311 A1 * | 1/2004 | Shchervinsky | A61M 1/84 |
| | | | 604/164.01 |
| 2005/0192548 A1 | 9/2005 | Dolliver et al. | |
| 2005/0197639 A1 * | 9/2005 | Mombrinie | A61M 1/84 |
| | | | 604/317 |
| 2007/0010798 A1 | 1/2007 | Stoller et al. | |
| 2012/0238972 A1 | 9/2012 | Karpowicz et al. | |
| 2013/0053793 A1 * | 2/2013 | Locke | A61M 1/92 |
| | | | 137/15.01 |
| 2016/0310711 A1 | 10/2016 | Luxon et al. | |
| 2017/0266031 A1 * | 9/2017 | Sanchez | A61F 5/4404 |

OTHER PUBLICATIONS https://www.ohmedical.com/External-Catheters/DRYDOCtrade-VACUUM-STATION--DD15/, 2020, 2 pages.
https://sageproducts.com/primafit-external-urine-management-system-for-females/, 2020, 3 pages.

* cited by examiner

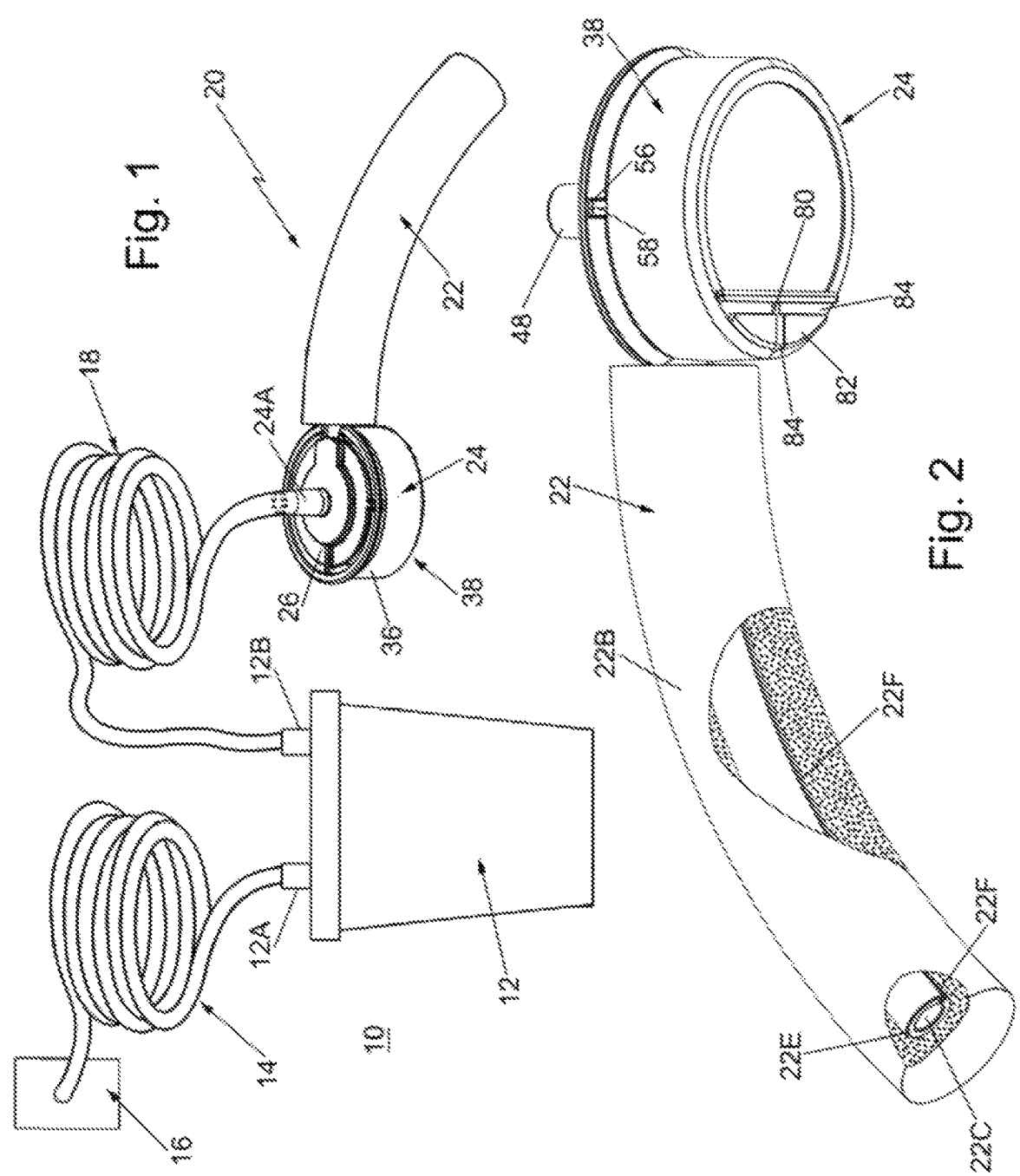

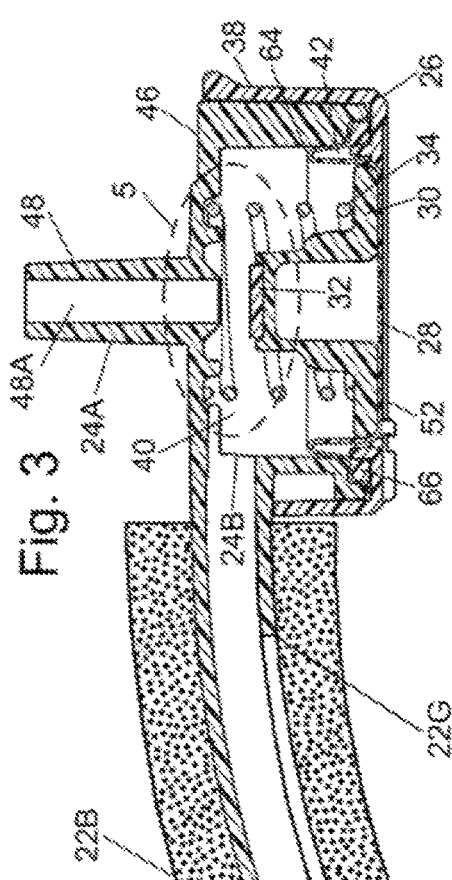
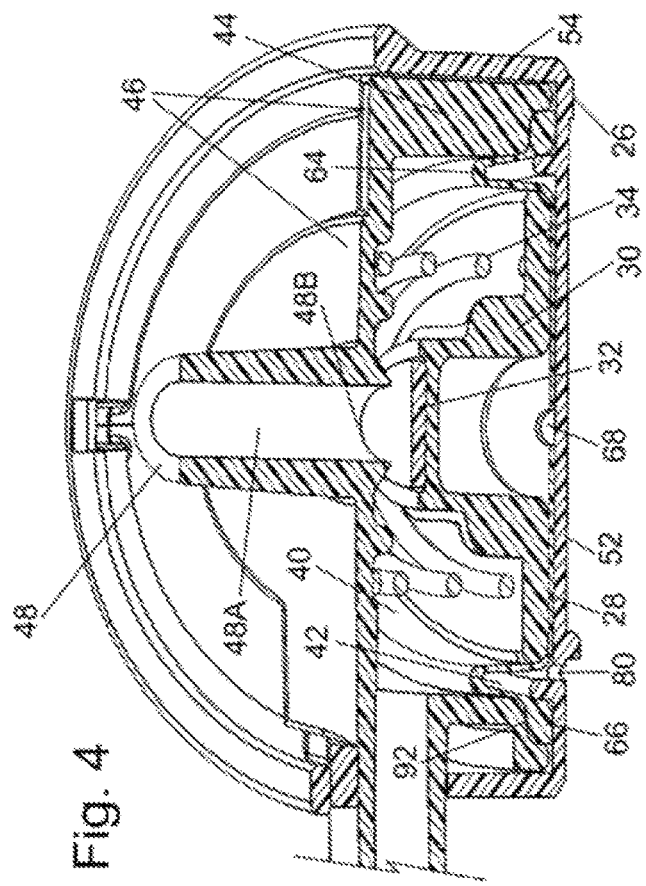
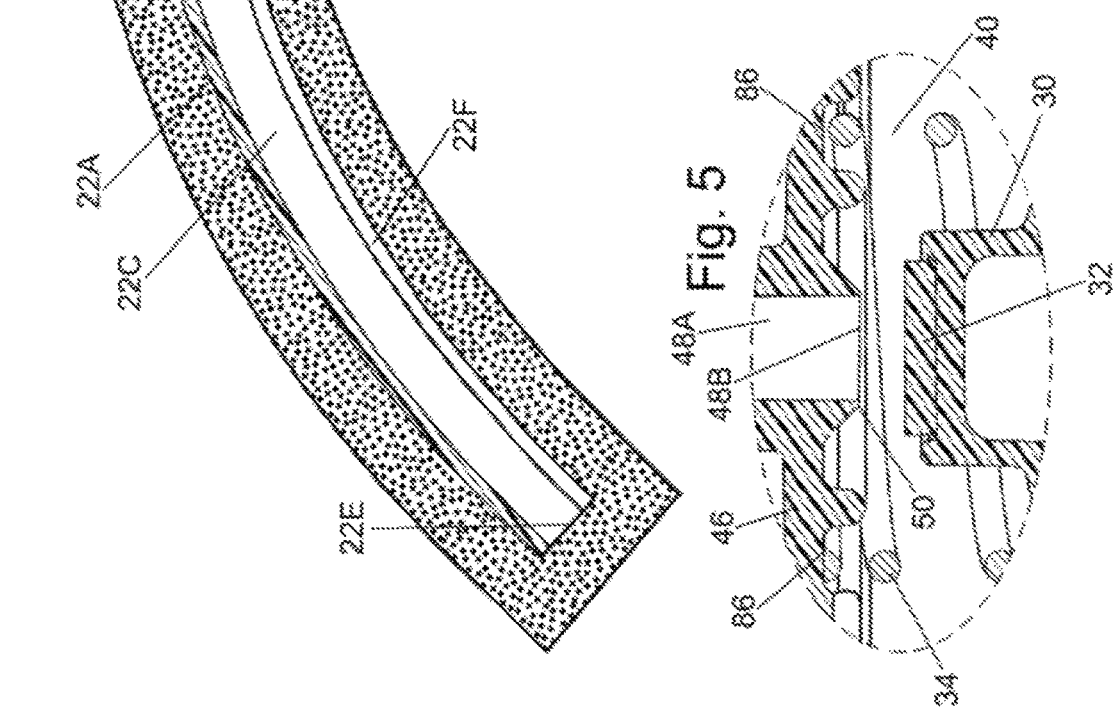

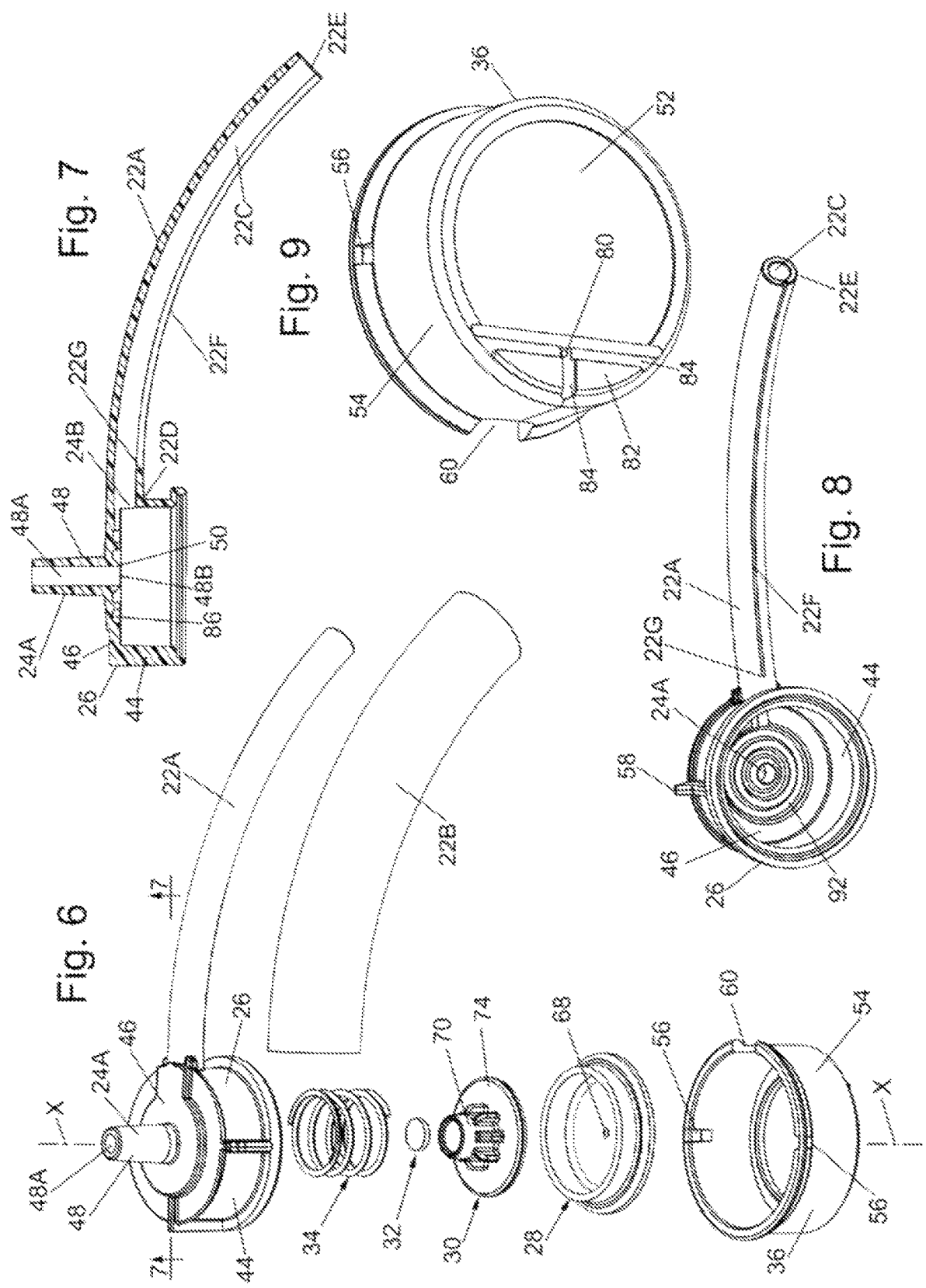

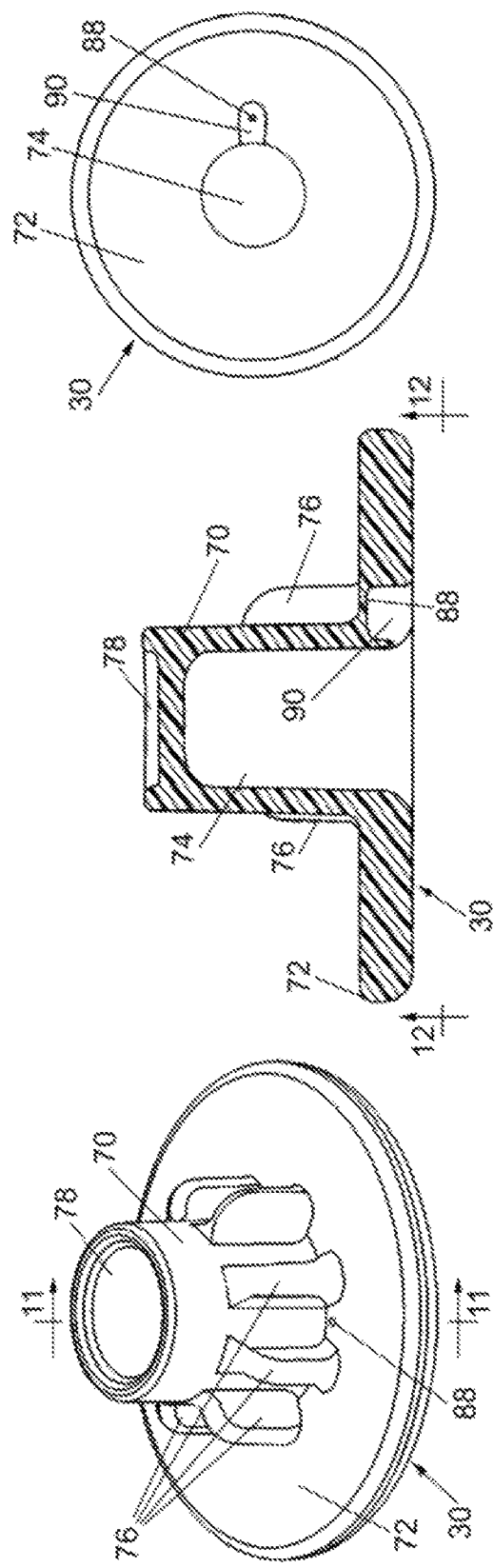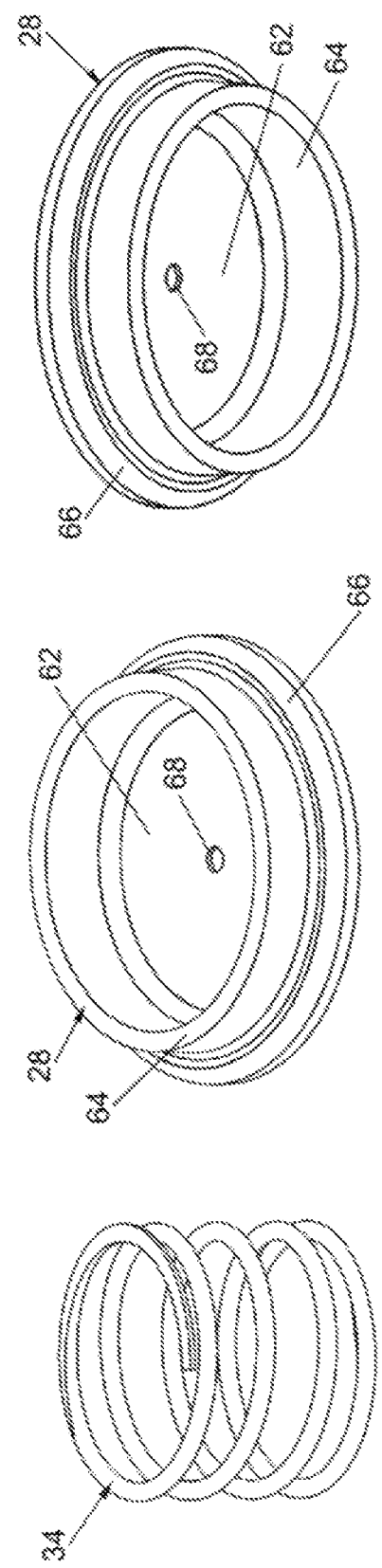

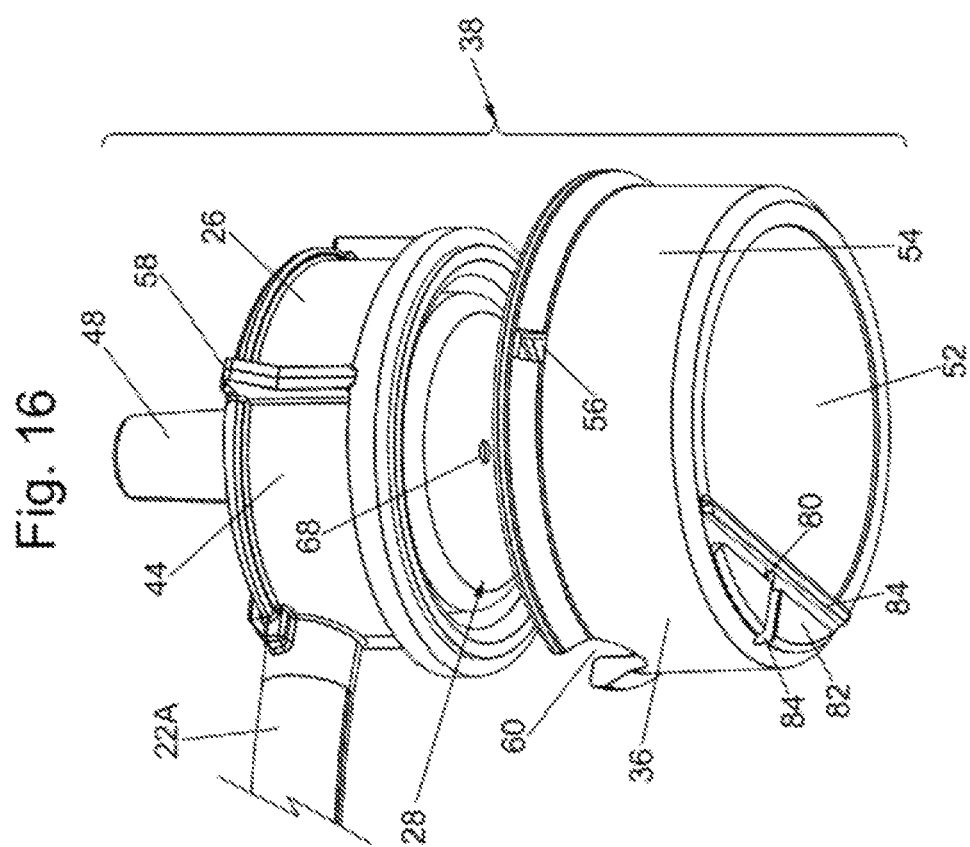

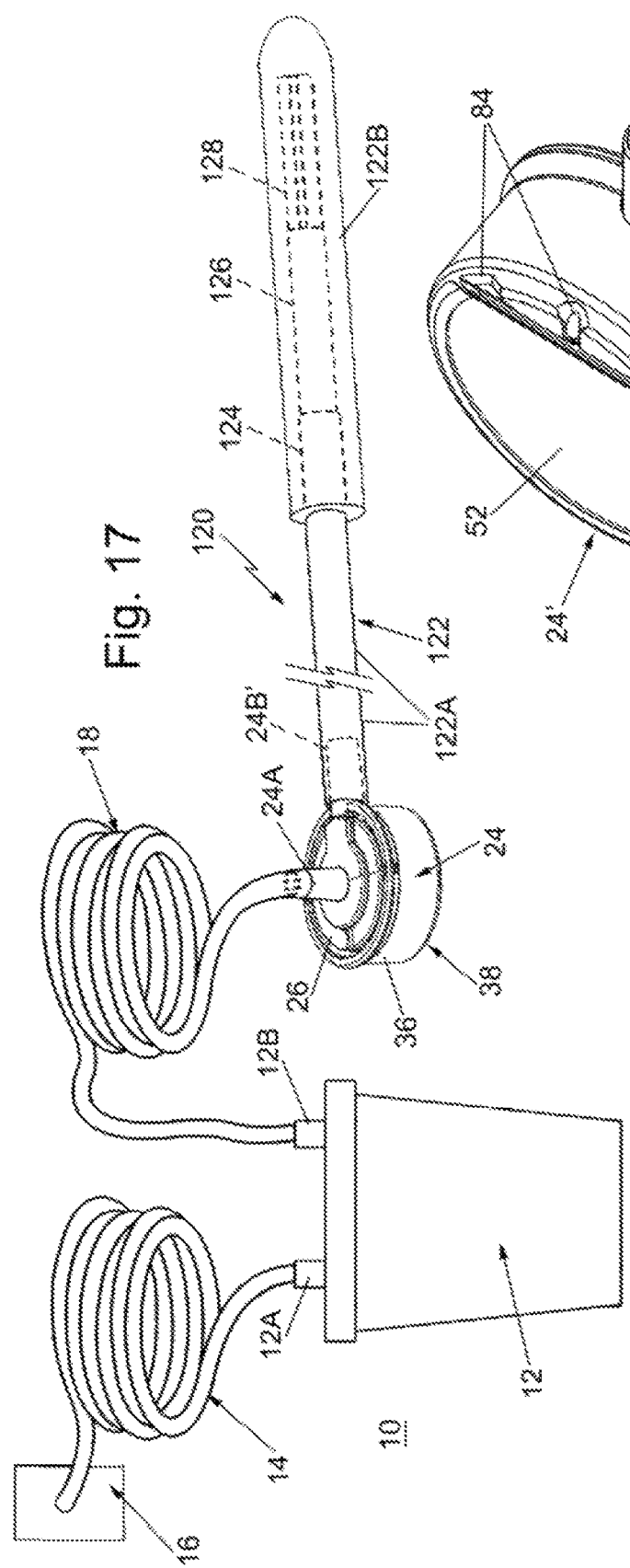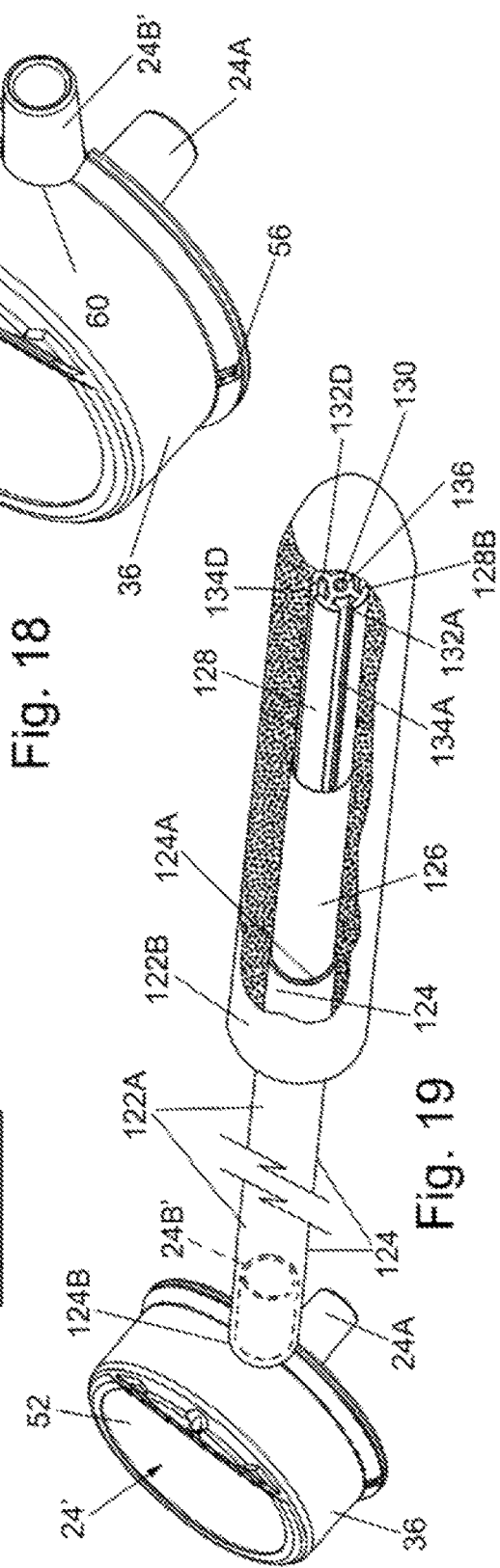

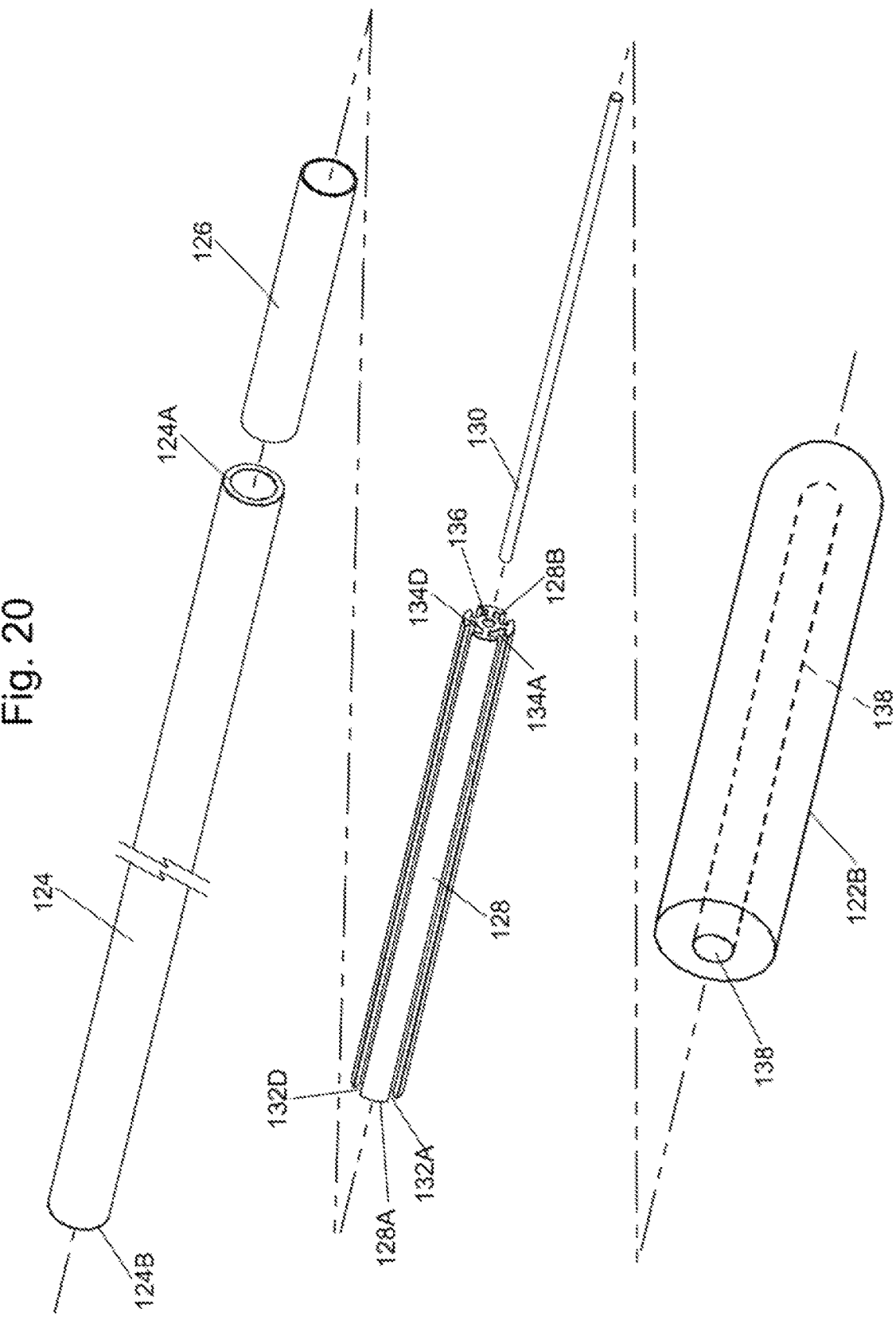

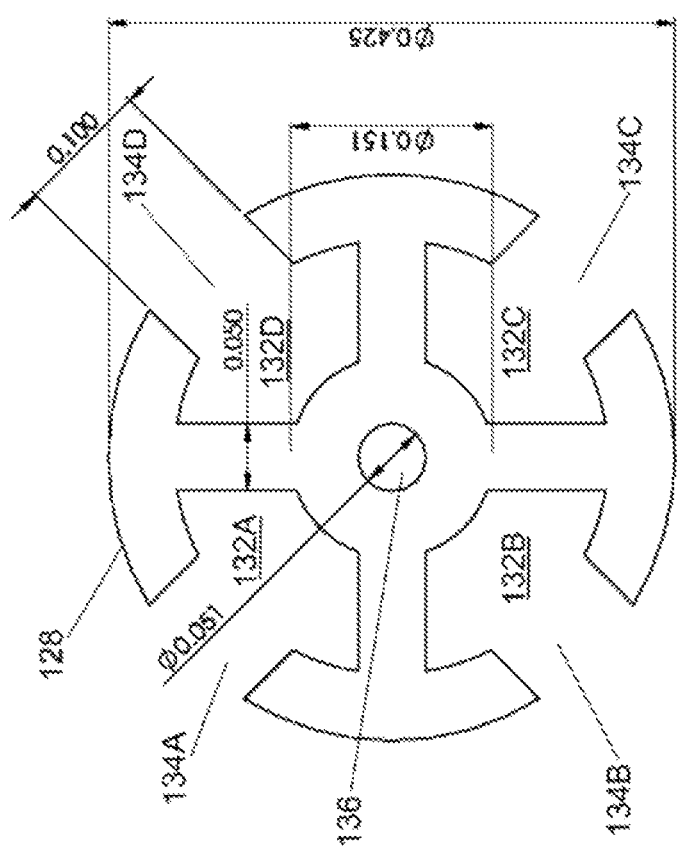

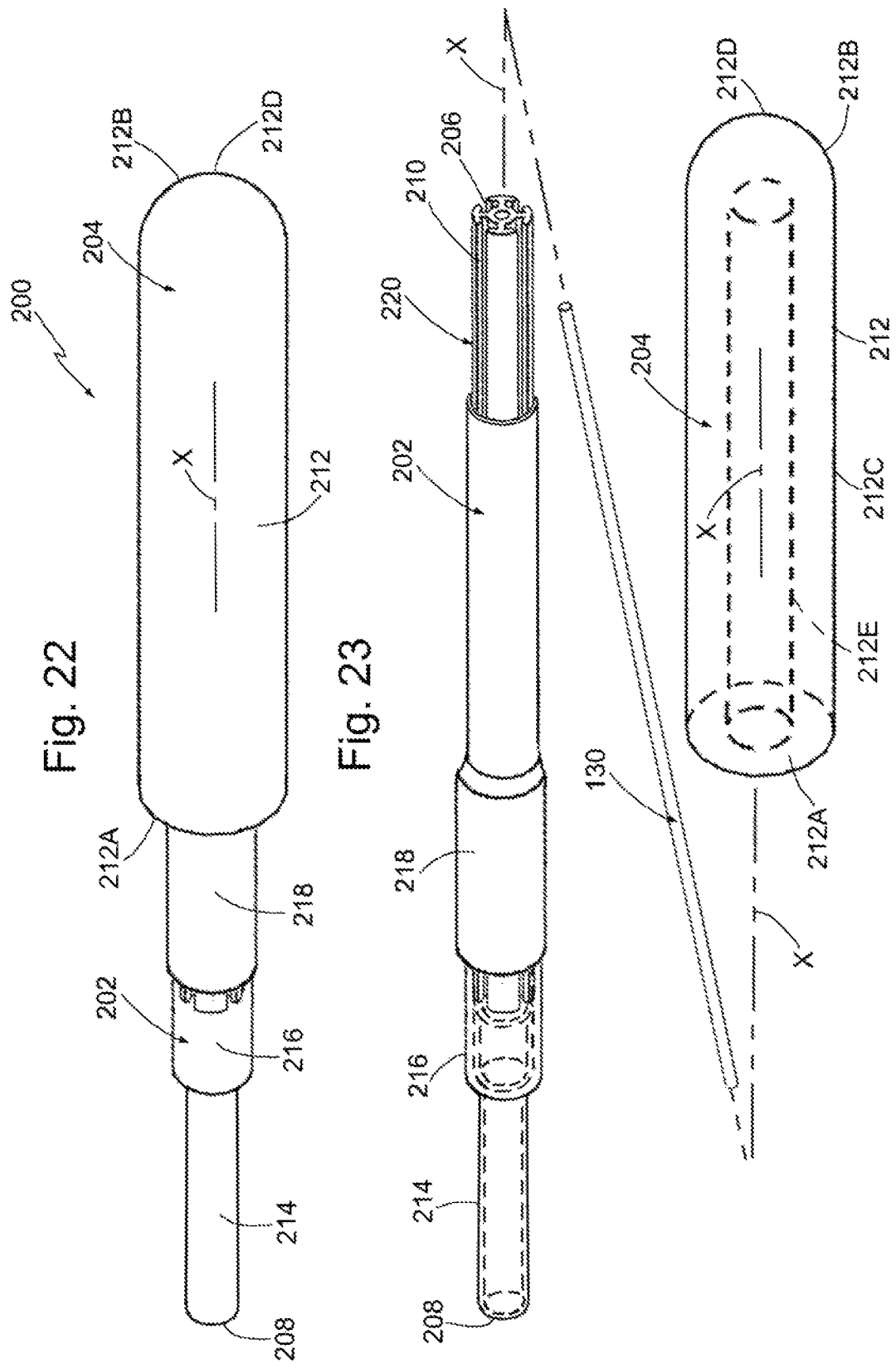

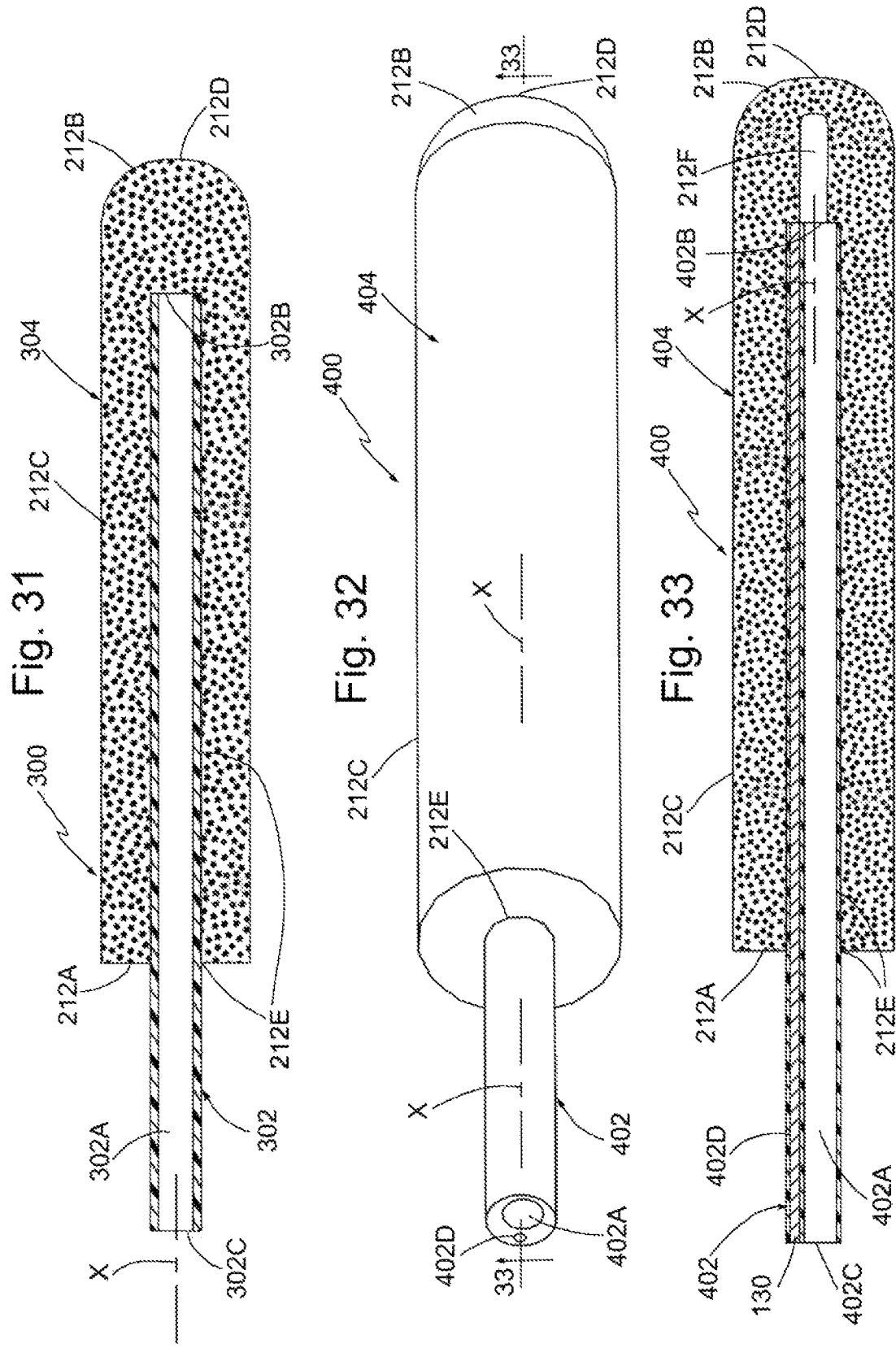

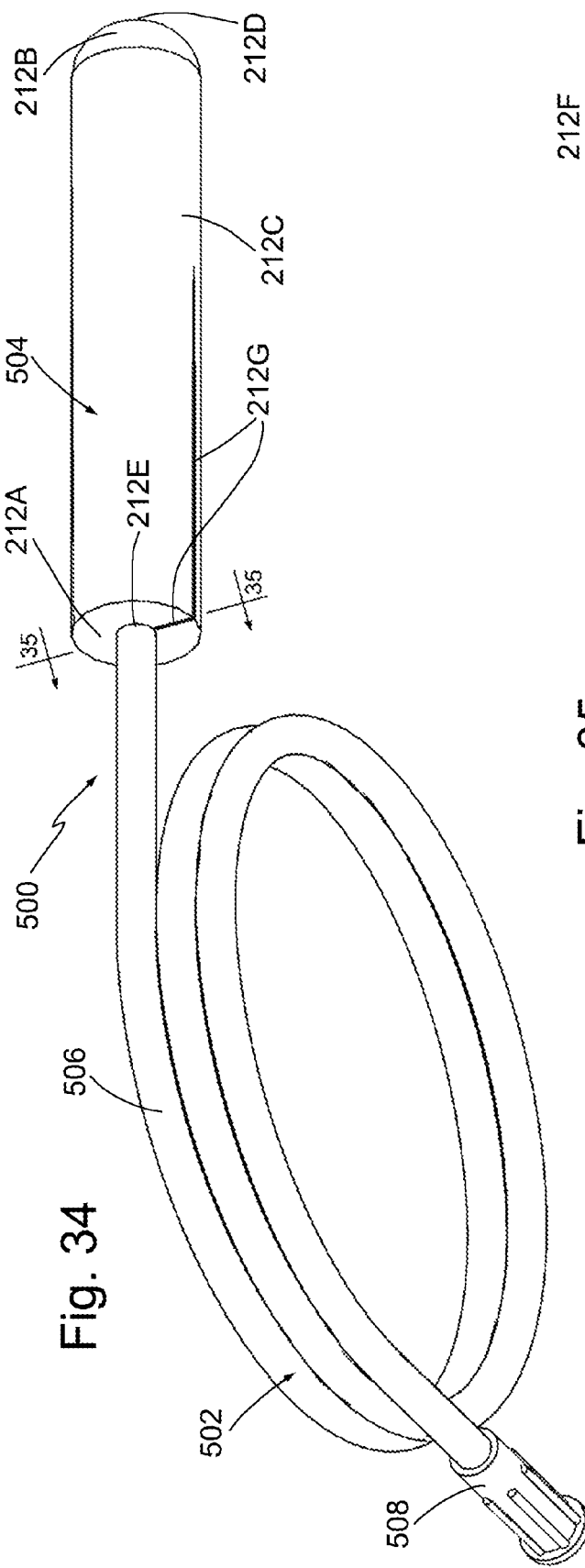
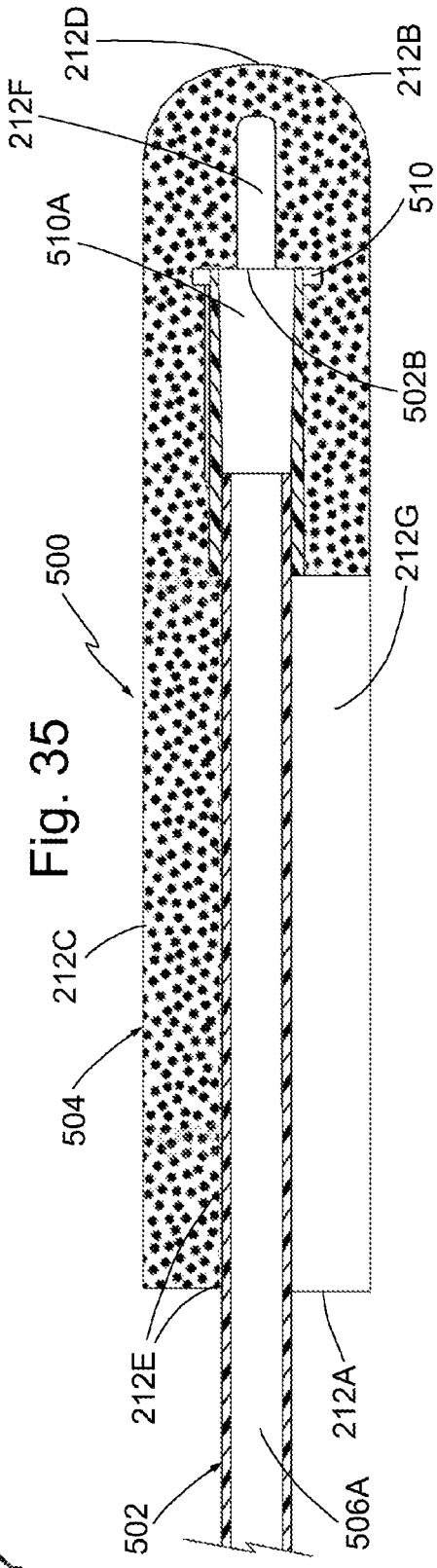

LEAKAGE RESISTANT EXTERNAL FEMALE CATHETER SYSTEM AND METHOD OF USE

CROSS-REFERENCE TO RELATED APPLICATIONS

This application is a Continuation-in-Part of U.S. patent application Ser. No. 16/996,214, filed on Aug. 18, 2020, entitled External Female Catheter System With Integrated Suction Regulator And Method Of Use, which claims the benefit under 35 U.S.C. § 119(e) of Provisional Application Ser. No. 62/924,326, filed on Oct. 22, 2019, entitled "External Female Catheter System With Integrated Suction Regulator And Method Of Use". The entire disclosure of both of said applications are specifically incorporated by reference herein for all purposes.

SPECIFICATION

Field of the Invention

This invention relates generally to medical devices and methods and more particularly to devices and methods for automatically removing urine from a female patient using suction applied to an external catheter.

Background of the Invention

Various external catheters are available for non-invasive urine output management in female patients. The PUREWICK® female external catheter available from C.R. Bard, Inc. is an example of one such device. That external catheter is a soft member having a hollow flexible body including a side opening exposing soft absorbent gauze. The catheter is configured to be positioned so that soft gauze is disposed between the patient's separated gluteus and labia and in fluid communication with the urethral opening of the patient, whereupon urine voided by the patient is wicked into the gauze. The catheter is arranged to be attached via suction tubing to a suction canister, which should in turn be connected to either a suction regulator on a hospital wall or a portable suction pump, such as the DRYDOC™ vacuum suction station of C.R. Bard, Inc., whereupon the urine wicked into the external catheter is carried by the suction into the canister for collection. The Instructions for Use (IFU) of the PUREWICK® female external catheter indicates that the suction source should be set to a minimum of 40 mmHg continuous suction.

Sage Products, LLC, now a Stryker Corporation company, provides an external urine management system for females under the trademark PRIMAFIT. That system is in many respects similar to the PUREWICK® system. In particular, the PRIMAFIT system basically comprises an external catheter body having an end cap to fit in the woman's perineal area to secure the catheter in place. The catheter includes soft wicking fabric that absorbs and diverts urine away from the patient's skin. Urine is then absorbed into the system's core and suctioned into a collection canister.

The patent literature includes various systems and methods for collecting and transporting urine away from a person's body, such as: U.S. Pat. No. 4,610,675 (Triunfol); U.S. Pat. No. 4,747,166 (Kuntz); U.S. Pat. No. 5,678,564 (Lawrence et al.); U.S. Pat. No. 5,894,608 (Birbara); U.S. Pat. No. 6,849,065 (Schmidt et al.); U.S. Pat. No. 7,018,366 (Easter); U.S. Pat. No. 7,220,250 (Suzuki et al.); and U.S. Pat. No. 8,287,508 (Sanchez).

As will be appreciated by those skilled in the art, most hospital suction regulators provide insufficient flow at low vacuum pressures, like the 40 mmHg recommended for use with the PUREWICK® female external catheter. Therefore nurses or other care givers frequently increase the vacuum to get adequate urine flow. However, the use of higher vacuum pressure poses an increased risk to the patient, as the only opening in the circuit for air to relieve the pressure is adjacent the patient's genitalia. Accordingly, use of increased vacuum pressure to increase the flow rate of urine being withdrawn into the canister runs the risk of injury to the delicate issue adjacent the urethral opening.

In our U.S. Provisional Patent Application Ser. No. 62/829,731, filed on Apr. 5, 2019, entitled System Including Suction Regulator For Automatically Removing Urine From A Female Patient And Method Of Use Of The System, which is assigned to the same assignee as this invention, there is disclosed and claimed a disposable suction regulator configured for use between the female external catheter and a canister coupled to a source of higher suction, e.g., a regulator at the hospital's suction line. That external catheter suction regulator is designed in such a way that it allows far greater flow at low pressures than do the traditional wall regulators. As such, it provides an efficient means for removing urine from a patient using an external catheter, wherein the flow rate is sufficiently high for increased effectiveness, yet is produced by a suction level that is sufficiently low to minimize the danger of injury to the delicate tissue of the patient adjacent the patient's urethral opening.

All of the references as cited herein are specifically incorporated by reference herein for all purposes.

The subject invention improves upon the invention of our aforementioned earlier filed provisional application various ways. One way is by providing an external female catheter and a suction regulator in an integral unit, which is simple in construction, low in cost, comfortable to use, and effective and safe in operation. Another aspect of the subject invention is an external catheter that does not include a suction regulator, i.e., it is not an integrated unit, so that it is even simpler in construction, low in cost, comfortable to use and effective and safe in operation.

SUMMARY OF THE INVENTION

One aspect of this invention is an external catheter configured to be coupled to a source of suction for removing by suction urine voided by a female. The external catheter comprises an elongated suction tube and a cover. The elongated suction tube has a longitudinal central axis, a distal end, a proximal end, and at least a first passageway extending longitudinally therethrough from the distal end to the proximal end. The proximal end is configured to be coupled to the source of suction. The distal end is open. The cover is formed of a body of moist hydrophilic polyurethane foam. The external surface comprises a proximal end surface, a distal end surface and an arcuate lateral surface interposed between the proximal end surface and the distal end surface. The distal end surface has an apex. The entire body is liquid permeable whereupon the arcuate lateral surface is liquid-permeable and extends around the longitudinal axis from the distal end surface to the proximal end surface. The cover is directly disposed over and about the elongated suction tube to enclose a section of the elongated suction tube contiguous with the open distal end thereof. The open distal end of the elongated suction tube is spaced from the apex. The cover is configured for external disposition with respect to the female, whereupon any portion of the liquid-permeable arcuate lateral surface is in fluid communication with a urethra opening of the female and with the cover being oriented so that the longitudinal axis of the cover is in a generally vertical orientation with the distal end surface being pointed downward so that urine voided by the female passes through a portion of the lateral surface and flows downward through the body of the cover into the at least a first passageway to be carried by suction from the at least a first passageway out of the external catheter for collection.

In accordance with one preferred aspect of the external catheter the distal end surface is arcuate.

In accordance with another preferred aspect of the external catheter the cover has a length in the range of 4 inches to 8 inches, and wherein the open distal end of the elongated suction tube is spaced by a distance of 0.25 inch to 3 inches from the apex.

In accordance with another preferred aspect of the external catheter the elongated suction tube comprises at least one continuous elongated slot extending longitudinally along the at least one first passageway for a length in the range of one inch to two inches from the open distal end. The at least one continuous elongated slot is in fluid communication with the at least one first passageway along an entire length of the at least one continuous slot and is in direct fluid communication with the cover along an entire length of the at least one continuous slot, whereupon when the external catheter is coupled to the source of suction, suction is applied down the at least one first passageway and through the at least one slot to draw urine through the cover into the at least one slot, and through the first passageway out of the external catheter for collection.

In accordance with another preferred aspect of the external catheter the elongated suction is malleable.

In accordance with another preferred aspect of the external catheter the elongated suction tube comprises at least three equidistantly spaced longitudinal passageways and at least three continuous elongated slots extending along the at least three equidistantly spaced longitudinal passageways.

In accordance with another preferred aspect of the external catheter the first section includes a central passageway surrounded by the at least three equidistantly spaced longitudinal passageways and a malleable wire extending through the central passageway.

In accordance with another preferred aspect of the external catheter the cover is five inches long.

In accordance with another preferred aspect of the external catheter the at least one continuous elongated slot and the at least one first passageway comprise an extrusion, and wherein the elongated suction tube additionally comprises a coupling tube and a heat shrink tube. The coupling tube has a distal portion into which a proximal end portion of the extrusion extends. The heat shrink tube is disposed over the distal portion of the coupling tube and over the extrusion but leaves a length of the at least one slot contiguous with the open distal end of the elongated suction tube uncovered and in direct fluid communication with the cover.

In accordance with another preferred aspect of the external catheter the elongated suction tube comprises a second passageway extending along the at least a first passageway from the distal end to the proximal end and a malleable wire extending through the second passageway.

In accordance with another preferred aspect of the external catheter the open distal end of the elongated suction tube is spaced by a distance in the range of 1 inch to 2 inches from the apex, and wherein the cover includes a hollow cavity extending along the longitudinal central axis from the open distal end of the elongated suction tube to a point in the range of 0.125 inch to 1.5 inches from the apex.

In accordance with another preferred aspect of the external catheter the elongated suction tube comprises a tubular coupler and a flexible tube. The tubular coupler has a central passageway. The flexible tube has a central passageway. The tubular coupler has a distal end and a proximal end in which a distal end of the flexible tube is fixedly secured. The distal end of the tubular coupler forms the open distal end of the suction tube.

In accordance with another preferred aspect of the external catheter the cover includes a bore extending along the longitudinal central axis from the proximal end surface and a slit extending from the proximal end of the cover to a point adjacent the proximal end of the tubular coupler and in communication with the bore. The slit provides access through which the tubular coupler and the contiguous portion of the flexible tube is inserted laterally.

In accordance with another preferred aspect of the external catheter the distal end of the tubular coupler is spaced by a distance in the range of 1 inch to 2 inch from the apex, and wherein the cover includes a hollow cavity extending along the longitudinal central axis from the open distal end of the elongated suction tube to a point in the range of 0.125 inch to 1.5 inches from the apex.

In accordance with another preferred aspect of the external catheter the cover includes a first bore section extending from the proximal end surface of the cover to a first intermediate point, and a second bore section extending distally from the first bore section. The tubular coupler is located in the second bore section with a contiguous portion of the flexible tube being located in the first bore section.

In accordance with another preferred aspect of the external catheter the distal end of the tubular coupler is spaced by a distance in the range of 1 inch to 2 inch from the apex, and wherein the cover includes a hollow cavity extending along the longitudinal central axis from the distal end of the tubular coupler to a point in the range of 0.125 inch to 1.5 inches from the apex.

Another aspect of this invention is a method for automatically removing by suction urine voided by a female patient. The method comprises providing an external catheter. The external catheter comprises an elongated suction tube and a cover. The elongated suction tube has a longitudinal central axis, a distal end, a proximal end, and at least a first passageway extending longitudinally therethrough from the distal end to the proximal end. The cover is formed of a body of which is entirely liquid-permeable and which has a longitudinal axis and an external surface comprising a proximal end surface, a distal end surface and an arcuate lateral surface interposed between the proximal end surface and the distal end surface, with an entire arcuate lateral surface being liquid-permeable. The cover is disposed with respect to the female, with the cover oriented so that the longitudinal axis of the cover is in a generally vertical orientation with the distal end surface being pointed downward whereupon any portion of the liquid-permeable arcuate lateral surface is in fluid communication with a urethra opening of the female. Suction is applied to the proximal end of the elongated suction tube, whereupon urine voided by the female passes through a portion of the arcuate lateral surface and flows downward through the body of the cover into the at least a first passageway to be carried by suction from the at least a first passageway out of the external catheter for collection.

In accordance with another preferred aspect of the method of this invention a receptacle or canister is coupled to the elongated suction tube to collect urine voided by the female.

In accordance with another preferred aspect of the method of this invention the body of the cover is formed of a moist hydrophilic polyurethane foam.

In accordance with another preferred aspect of the method of this invention suction is applied in a range 40-200 mmHg.

DESCRIPTION OF THE DRAWING

FIG. 1 is an illustration of one exemplary system for automatically removing urine from a female patient making use of an integrated unit having an external female catheter and suction regulator constructed in accordance with a first aspect of this invention and which can be used in a method of this invention;

FIG. 2 is an enlarged isometric view, partially in section, of the integrated external female catheter and suction regulator unit shown in FIG. 1;

FIG. 3 is an enlarged longitudinal sectional view of the integrated external female catheter and suction regulator unit shown in FIG. 2;

FIG. 4 is an enlarged sectional view of the suction regulator portion of the integrated external female catheter and suction regulator unit shown in FIGS. 2 and 3;

FIG. 5 is an enlarged sectional view of the portion of the suction regulator shown within the area designated by the broken line oval designated by the reference number 5 in FIG. 3;

FIG. 6 is an exploded isometric view of the various components making up the integrated external female catheter and suction regulator unit shown in FIGS. 2 and 3;

FIG. 7 is a reduced size longitudinal sectional view of one component, i.e., a body portion and an integrated suction tube, forming a portion of the integrated external female catheter and suction regulator unit shown in FIGS. 2 and 3;

FIG. 8 is a reduced size isometric view of the component of the integrated external female catheter and suction regulator unit shown in FIG. 7;

FIG. 9 is an enlarged isometric view of another component, i.e., a cap member, of the integrated external female catheter and suction regulator unit shown in FIGS. 2 and 3;

FIG. 10 is an enlarged isometric view of another component, i.e., a piston, of the integrated external female catheter and suction regulator unit shown in FIGS. 2 and 3;

FIG. 11 is a sectional view taken along line 11-11 of FIG. 10;

FIG. 12 is a reduced plan view taken along line 12-12 of FIG. 11;

FIG. 13 is an enlarged isometric view of another component, i.e., a biasing spring, of the integrated external female catheter and suction regulator unit shown in FIGS. 2 and 3;

FIG. 14 is an enlarged isometric view of another component, i.e., a diaphragm, of the integrated external catheter and suction regulator unit shown in FIGS. 2 and 3;

FIG. 15 is an enlarged isometric view of the diaphragm of FIG. 14 but taken from a different angle;

FIG. 16 is an enlarged isometric view showing the assembly of the cap member of FIG. 9 to the body portion and integrated suction tube component of FIGS. 7 and 8 to complete the assembly of the integrated external female catheter and suction regulator unit shown in FIGS. 2 and 3;

FIG. 17 is an illustration, similar to FIG. 1, but showing another exemplary system for automatically removing urine from a female patient constructed in accordance with the first aspect of the invention and making use of a more preferred integrated unit having an external female catheter and suction regulator constructed in accordance with this invention and which can be used in a method of this invention;

FIG. 18 is an isometric view of an alternative suction regulator forming a portion of the more preferred integrated unit shown in FIG. 17;

FIG. 19 is an enlarged isometric view, partially in section, of the integrated external female catheter and suction regulator unit shown in FIG. 17;

FIG. 20 is an enlarged exploded isometric view of another portion of the integrated external female catheter and suction regulator unit shown in FIG. 17;

FIG. 21 is a greatly enlarged end view of one of the components, i.e., a multi-slot end-piece, making up a portion of the integrated external female catheter and suction regulator unit shown in FIG. 17;

FIG. 22 is an isometric view of one exemplary external catheter constructed in accordance with a second aspect of this invention, wherein the external catheter is not part of an integrated system including an integrated suction regulator such that it can be used by itself with any appropriate source of suction and, if desired, any receptacle or canister for collecting urine from the female patient;

FIG. 23 is an exploded isometric view of the external female catheter shown in FIG. 22;

FIG. 31 is a sectional view taken along line 31-31 of FIG. 30;

FIG. 32 is an isometric view of still another exemplary external catheter constructed in accordance with the second aspect of this invention, wherein the external catheter is not part of an integrated system including an integrated suction regulator such that it can be used by itself with any appropriate source of suction and, if desired, any receptacle or canister for collecting urine from the female patient;

FIG. 33 is a sectional view taken along line 33-33 of FIG. 32;

FIG. 34 is an isometric view of yet another exemplary external catheter constructed in accordance with the second aspect of this invention, wherein the external catheter is not part of an integrated system including an integrated suction regulator such that it can be used by itself with any appropriate source of suction and, if desired, any receptacle or canister for collecting urine from the female patient;

FIG. 35 is a sectional view taken along line 35-35 of FIG. 34;

DETAILED DESCRIPTION OF THE PREFERRED EMBODIMENT

Figure 24:
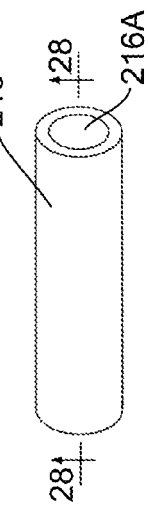
FIG. 24 is an isometric view of one of the components, i.e., a heat shrink tube, forming a portion of the external catheter shown in FIGS. 22 and 23.

Referring now to the various figures of the drawing wherein like reference characters refer to like parts, there is shown in FIG. 1 one exemplary embodiment of a system 10 including an integrated external female catheter and suction regulator unit 20 constructed in accordance with one exemplary preferred embodiment of this invention for automatically removing urine from a female patient.

The details of the integrated external female catheter and suction regulator unit 20 will be described later. Suffice it for now to state that the unit 20 basically comprises an external catheter 22 and a suction regulator 24 which when assembled together form an integrated (one-piece) unit. The external catheter 22 portion of the unit 20 basically comprises a suction tube 22A and a removable liquid permeable cover 22B. The cover 22B is disposed over and surrounding the suction tube 22A. When the unit 20 is in use the cover 22B placed against the urethra opening of a female patient to serve as a urine wicking member to receive urine which has been excreted by the patient. The suction regulator 24 portion of the unit 20 serves to provide a suitable safe regulated level of suction to the external catheter to effectively draw urine from the cover 22B through a longitudinally extending slot (to be described later) in the suction tube 22A into and through the suction regulator 24 to deliver it to a receptacle or canister 12, which forms a portion of the system 10.

The receptacle or canister 12 is of conventional construction and includes a port 12A that is configured to be connected, via a section of conventional tubing 14, to a suction source, e.g., a wall regulator 16 of the hospital's main suction line which provides suction to the suction regulator 24. The wall regulator 16 should be set to line vacuum or the maximum available vacuum pressure if a line function is not available. The canister 12 includes another port 12B, which is connected, via another section of conventional tubing 18, to a "line suction port" 24A, of the suction regulator 24. The suction regulator 24 includes another port, which is internal and hereinafter identified as the "regulated suction port" 24B, which is connected to and in fluid communication with the proximal end of a suction tube 22A.

As will also be described later the suction regulator 24 is configured to enable flow through it from the external catheter to the canister nearing the maximum the hospital's suction line or regulator 16 is capable of sustaining without allowing the pressure to rise above a desired operating value, e.g., 40 mm Hg, of the suction regulator 24 in the event the external catheter becomes sealed against the patient. Since the suction regulator 24 is located between the external catheter 22 and the urine collecting canister or receptacle 12, the regulator 24 will be closer to the catheter 22 than if it was located between the canister or receptacle 12 and the hospital suction line or regulator 16, thereby enabling the maximum possible urine flow, but necessitates the urine flowing through the regulator. To that end, the entire unit 20 is intended to be a non-sterile, single-patient-use disposable unit.

Turning now to FIGS. 2, 3, 7 and 8, the details of the external catheter portion 22 will now be described. As mentioned above it basically comprises the suction tube 22A and the liquid permeable cover 22B. The suction tube 22A is an elongated arcuate member having a central passageway 22C extending the length thereof from its proximal end 22D to its distal end 22E. The distal end 22E is open. The proximal end 22D is also open and forms the heretofore identified internal port 24B (FIG. 3) of the suction regulator. The proximal end of the suction tube is secured to a portion of a housing assembly (to be described later) of the suction regulator. That portion of the housing assembly constitutes a hollow housing body 26. As best seen in FIGS. 7 and 8, the suction tube 22A includes a longitudinally extending slot 22F extending approximately the entire length thereof from a point 22G adjacent the housing body 26 to the distal end 22E. The slot is in fluid communication with the central passageway 22C of the suction tube 22 along the entire length of the slot. The portion of the suction tube 22A that includes the slot 22F constitutes a first or distal section of the suction tube, and the portion of the suction tube that is connected to the portion of the housing assembly constitutes a second or proximal section of the suction tube.

The cover 22B is a cylindrical member formed of a liquid permeable material, preferably one that is absorbent and hydrophilic, e.g., a polyurethane or a PVA (polyvinyl alcohol) sponge, although it could be formed of other liquid permeable materials such as, cellulose, polyurethane, gauze, etc. As best seen in FIG. 2 the cover 22B includes a central passageway extending from its proximal end to a point adjacent its distal end. The internal diameter of the central passageway of the cover 22B is approximately the same size or slightly smaller than the external diameter of the suction tube 22A so that the suction tube can be located therein, with the cover held thereon by friction, whereupon the closed distal end of the cover closes the open distal end 22E of the suction tube. Moreover, the cover extends the entire length of the suction tube up to a point immediately adjacent the housing body 26. Accordingly, when regulated suction produced by the suction regulator 24 (as will be described later) is applied at the port 24B that regulated suction will appear along the length of the slot 22F to draw any urine that the female patient voided into the cover from there into the slot whereupon that urine will be pulled into the passageway 22C and carried by air from through that passageway to the suction regulator 24. From there the urine is carried to the receptacle or canister 12. In particular, with the system 10 as described above when suction is applied from the hospital's suction line or wall regulator 16, that high level of suction is conveyed through the tubing section 14, from whence it is applied to the canister or receptacle 12 and the associated tubing section 18 to the line suction port 24A of the suction regulator 24, whereupon it is regulated (e.g., reduced) by operation of the suction regulator to a much lower operating level, e.g., 40 mmHg. That reduced or regulated suction will appear on the suction port 24B of the regulator 24 and from there to the external catheter 22 to thereby draw urine from the external catheter 22 back through the regulator 24, and out through the tubing section 18 into the receptacle or canister 12 for collection therein.

It should be noted that for many applications the operating level is preferably approximately 40 mmHg. However, that level could be raised up to approximately 200 mmHg, since some hospitals are comfortable with higher vacuum pressures. If desired the system 10 may also include an overflow detector of any suitable construction to provide an indication that the amount of urine within receptacle has reached a predetermined threshold, e.g., is about to overflow, and/or to provide a signal to a controller (not shown) stop to halt the operation of the system so that no further urine is drawn into the receptacle until it can be emptied. For example, the canister 12 may include a shut off float valve and/or a filter at outlet 12A to prevent possible contamination of the hospital's main suction.

As should be appreciated by those skilled in the art from the discussion to follow the operation of the suction regulator 24 ensures that a desired level of suction is applied to the external catheter 22 to ensure proper and safe operation of the system, i.e., to maximize the rate at which urine may be withdrawn from the catheter into the receptacle or canister without subjecting the delicate tissue of the woman at her urethra opening to injury, e.g., a hematoma, from excess suction thereat.

Turning now to FIGS. 3-6, the construction of the suction regulator portion 24 of the unit 20 will now be described. To that end as can be seen the suction regulator 24 basically comprises a flexible diaphragm 28, a piston 30, a sealing disk 32, a helical compression spring 34, and a housing assembly 38. The housing assembly 38 is made up of the heretofore identified housing body 26 and a lid or cover 36. The lid or cover 36 and the housing body 26 are configured to be connected together, as will be described later and as shown in FIG. 16, to form the hollow housing assembly 38. That assembly encloses (houses) the other components making up the suction regulator 24. The housing body 26 and the cover 36 are preferably formed of a rigid plastic, such as ABS, although other plastics can be used. The suction tube 22A, being integral with the housing body 26 is also formed of the same material as the housing body, but could be formed of some other material. That other material may be chosen to exhibit some degree of flexibility to enhance engagement of the external catheter 22 with the portion of the female's body contiguous with her urethra opening As best seen in FIGS. 3-8 the housing assembly 38 defines two internal chambers, namely, an upper chamber 40 and a lower chamber 42, which are separated from each other by a portion of the diaphragm 28. The housing body 26 includes a circular annular sidewall 44 projecting downward from a top wall 46. The circular sidewall 44 extends about a central axis X (FIG. 6) of the suction regulator. A tubular extension 48 extends upward from the top wall and centered on the axis X. The tubular extension forms the heretofore identified line suction port 24A and includes a passageway 48A extending through it. The lower end of the passageway 48A is open at 44B, with the portion of the top wall 46 contiguous with the opening 48B forming a beveled or conical surface valve seat 50 (FIG. 5). The opening 44B is in fluid communication with the upper chamber 40 in the interior of the housing assembly 38 of the suction regulator 24. The upper or free end of the passageway 48A is open and configured so that the distal end of the tubing section 18 can be connected to it, whereupon the passageway extending through that tubing section will be in fluid communication with interior of the housing assembly 38 and with upper chamber 40.

The lid or cover 36 is a generally cup-shaped member having a generally planar bottom wall 52 and a circular annular sidewall 54 projecting upward therefrom. The sidewall 54 includes a pair of diametrically opposed notches 56 immediately adjacent the lower edge of the sidewall. As can be seen in FIG. 16 the notches 56 are configured to receive respective diametrically opposed projecting tabs 58 of the housing body 26 to secure the lid or cover 36 to the housing body 26 and thus complete the housing assembly 38. The sidewall 54 of the lid or cover 36 also includes an arcuate recess 60 (FIG. 9) in the edge of the sidewall located midway between the notches 56. The recess 60 serves to receive the suction tube 22A when the lid or cover 36 is secured to the housing body 26.

The diaphragm 28 is best seen in FIGS. 14 and 15, and is preferably a rolling diaphragm formed of any resilient flexible material, e.g., silicone, nitrile, etc. The diaphragm includes a generally planar circular central portion 62 and a folded generally V-shaped or U-shaped edge portion 64 surrounding the central portion and terminating in a flanged generally planar thickened periphery 66. A small opening or hole 68 is located in the center of the central portion 62. The central portion 62 is disposed on a planar top surface of the piston 30 (to be described later), with the thickened periphery 66 of the diaphragm disposed on an annular ledge 92 (FIG. 4) at the lower end of the sidewall 44 of the housing body 26 between that ledge and the inner surface of the bottom wall of the lid or cover 36. With the lid or cover secured to the housing base 26 the thickened periphery 66 of the diaphragm 28 is tightly sandwiched between the ledge and the inner surface of the lid or cover. This arrangement divides the interior of the suction regulator into the heretofore identified upper chamber 40 and lower chamber 42. In particular, the upper chamber is formed between the inner surface of the top wall 46 of the body member 26, the contiguous inner surface of the sidewall 44 of the body member, the upper surface of a portion of the diaphragm 28 and a portion of the piston 30. The lower chamber 42 is formed between the inner surface of bottom wall 52 of the lid or cover 36, and the central portion 62 and contiguous V or U-shaped portion 64 of the diaphragm 28.

The piston 30 is best seen in FIGS. 10 and 11 and basically comprises a unitary body formed of a rigid plastic, such as ABS. The body includes a central hub 70 whose bottom end terminates in a circular flange 72. The bottom surface of the flange is planar, but includes a circular recess 74 in the center thereof and extending into the hub 70. A plurality of ribs 76 extend outward radially from the hub and serve to reinforce the flange 72 and to center the biasing spring 34 about the central axis X. The top surface of the hub 70 includes a recess 78 for receipt of the sealing disk 32.

The sealing disk 32 is fixedly secured in the recess 78 of the piston 30 and serves as a valve member to engage the valve seat 50 in the upper chamber 40 when excess suction is applied (as will be described later). The sealing disk 32 is formed of any suitable material, e.g., silicone rubber.

The cover or lid 36 includes a small opening or vent (FIGS. 2, 4, 9 and 15) to the ambient atmosphere which will be referred to as the "atmospheric reference port" 80. The atmospheric reference port ensures that the lower chamber 42 will be at the pressure of the ambient atmosphere. In particular, the port 80 extends through the thickness of the cover and is in fluid communication with the interior of lower chamber 42 to maintain that chamber at atmospheric pressure. Inasmuch as the atmospheric reference port 80 is located in the bottom surface of the cover 36, it is susceptible to being blocked or covered by a sticker, some other object or even a portion of the female's body. To prevent such an occurrence the lid or cover is shaped to prevent blockage of the port 80. In particular, the lid or cover includes a thickened portion 82 located adjacent the port 80 with an elongated shallow tripartite or T-shaped recess or slot 84 extending into the thickened portion. The outer edge of the atmospheric reference port 80 is located at the bottom of the slot 84 at the intersection of the slot's various three sections and is in fluid communication with each of those sections. The outer end of each of the slot sections is open. Thus, if something should be on the surface of the thickened portion 82 of the lid or cover disposed over the atmospheric reference port 80 air can still enter into that port via any open end of the T-shaped slot 84.

A label (not shown) bearing indicia or information regarding the unit 20 may be fixedly secured within a very shallow recess 96 in the outer surface of the lid or cover adjacent the thickened portion 82 so its presence does not block the T-shaped slot 84.

The biasing spring 34 is a helical compression spring formed of any suitable material, e.g., stainless steel. As best seen in FIGS. 3-6 and 13, the spring is located within the upper chamber 40, with the lower end of the spring in engagement with the undersurface of the flanged portion 72 of the piston 30 and surrounding a piston's central hub 70 and with the upper end of the spring located within an annular recess 86 (FIG. 5) in the undersurface of the top wall 46 of the housing body 26. The spring is under compression to bias the piston and diaphragm downward and away from the valve seat 50.

As mentioned above, the suction regulator 24 regulates the level of suction to a desired operating value and provides the regulated suction to the external catheter (the urine wicking member) 22. To that end, the regulator 24 is configured to limit the amount of suction applied to the external catheter to that desired value even if a level of suction greater than that predetermined value is applied to the suction regulator from the suction source (particularly if the suction source is at a much higher level, which will typically be the case if the suction source is the hospital's suction line). The predetermined or desired suction value (hereinafter referred to has the "regulator's set-point" or "regulated set-point value") is fixed and is factory-established by the spring 34 and dimensions of the housing body 26, the cover or lid 36, the piston 34 and the sealing disk 42. In this regard the pressure within the lower chamber 42 will be equal to atmospheric pressure by virtue of the communication of that chamber with the ambient atmosphere via the atmospheric reference port 80. With suction applied, the pressure within the upper chamber 40 will be lower than the atmospheric pressure within the lower chamber 42. The differential pressure between the chambers 40 and 42 will force the diaphragm 28 and the piston 30 upward toward the valve seat 50. The compression spring 34, however, will impart a counter force on the piston and diaphragm that opposes the differential pressure force, thereby forcing the piston upward such that the level of suction appearing at the regulated suction port 24B is the desired operating value.

If the suction applied via line suction port 24A is greater that the predetermined value or level the piston 30 and diaphragm 28 will move such that the sealing disk 32 on the piston's hub 70 comes into engagement with the valve seat 50, thereby isolating the upper chamber 40 from the suction appearing on the line suction port 24A. This action thereby limits the level of suction in upper chamber and hence at external catheter 22 to the predetermined level (operating value). If, however, the suction applied via line suction port 24A is less than the predetermined operating level the piston and diaphragm will only move part of the way downward. As such the level of suction applied to the line suction port 24A will equal that in the regulated suction port 24B and that applied to the external catheter 22.

It should be pointed out at this juncture that the suction regulator 26 is also configured to prevent the sealing disk 32 on the piston from becoming stuck for an extended period of time on the valve seat 50 in the event of what will be referred to hereinafter as an "over-travel situation". In this regard, if the suction regulator 24 is operated in a manner such that a high level of suction is applied very rapidly, the piston may experience an over-travel situation wherein it moves upward very quickly such that the sealing disk 32 becomes stuck on the valve seat 50. Under this condition the suction applied to the suction tube 24A of the external catheter would be at a higher level than the suction regulator 24 was set to provide. The suction regulator could thus stay in that state for an extended/indefinite period of time, particularly if the external catheter becomes blocked, e.g., its wicking portion (the sponge cover 24B) is in tight engagement with the vaginal tissue surrounding the urethral opening and not over the urethral opening itself. To prevent such an occurrence, the regulator 24 includes two "bleed" holes. One bleed hole is the heretofore-identified small hole 68 located in the center of the diaphragm 28. The second bleed hole is identified by the reference number 88 and is located in the piston 30. In particular, as best seen in FIG. 11A, the cylindrical cavity 74 in the piston contiguous with the bottom surface of the flanged portion 72 includes a radially extending recess 90. The bleed hole 88 is located in that recess and extends through the flanged portion of the piston. Since the bleed hole 68 in the diaphragm 28 is located in the center thereof, i.e., on the central axis X, it will overlie and be in fluid communication with the cylindrical cavity 74 in the piston. The recess 90 is in fluid communication with the cylindrical cavity 74. Thus, the bleed hole 88 in the piston will be in fluid communication with the bleed hole 68 in the diaphragm. Since the bleed hole 68 in the diaphragm is in communication with the lower chamber 42, that chamber will be in fluid communication with the upper chamber 40 via the communicating bleed holes 68 and 88. Hence, if the sealing disk 34 on the piston should become stuck on the valve seat 50, air which enters into the lower chamber 42 via the atmospheric reference port 80 can then pass through the bleed hole 88 into the cylindrical cavity 74, and from there through recess 90 into the bleed hole 88, from whence it will enter into the upper chamber 40. The ingress of air into the upper chamber will decrease the vacuum within that chamber, thus enabling the spring 34 to move the piston 30 downward so that the sealing disk 32 is off of the valve seat 50.

It must be pointed out at this juncture that the sealing disk 32 becoming stuck on the valve seat 50 may not be an issue. In such a case the diaphragm 28 need not include the bleed hole 68, and the piston 30 need not include the bleed hole 88 and the associated recess 90.

In accordance with one exemplary preferred embodiment of the suction regulator 24, inner diameter of the lower chamber 42 is approximately 1.5 inch. The inner diameter of the upper chamber 40 is approximately 1.5 inch. The spring is configured to naturally apply a bias force of approximately 1.0 pound. The inner diameter of the passageway 48A is approximately 0.25 inch. The opening 48B located within the bounds of the valve seat 50 is approximately 0.22 inch. The atmospheric reference port 80 is approximately 0.035 inch in diameter. The bleed hole 88 is approximately 0.016 inch in diameter. The bleed hole 68 is approximately 0.062 inch in diameter. Each tubing section 14 and 18 is conventional having an internal passageway of approximately 0.25 inch in diameter, and each section is approximately six feet in length, but could be shorter or longer depending upon the application. In any case with an integrated external female catheter and suction regulator unit 20 sized as just described, in a system like that described during typical operation the flow rate of air into the upper chamber 40 via bleed holes should be in the range of approximately 3 to 10 standard cubic feet per hour (SCFH). In fact, benchtop testing suggests that one version of the system 20 of this invention, making use of its disposable regulator 26 is capable of air flow rates up to 100 SCFH as compared to the 15 SCFH rate observed with some commercially available wall regulator set to the value of 40 mmHg. The additional flow allows for increased urine capture at the interface of the actual catheter, faster drying of the catheter (which helps prevent skin breakdown and infection) and pulls the urine through the tubing into the canister 30 more efficiently. This is especially true if the tubing drapes down below the height of the patient and canister.

The integrated external female catheter and suction regulator unit 20 of this invention is designed for use with a single female patient over a prolonged period of time and after use with that patient, it is to be disposed. The cover 22B is however designed to be replaced on the suction tube whenever necessary for that particular patient. To replace the cover 22B, all that is required is to remove the used cover from the suction tube 22A by pulling it in the distal direction and then replacing the used (soiled) cover with a fresh cover on the suction tube.

Turning now to FIG. 17 there is shown another and more preferred exemplary system 10' for automatically removing urine from a female patient making use of a more preferred integrated unit 120 having an external female catheter 122 and suction regulator 24' constructed in accordance with this invention and which can be used in a method of this invention.

The system 10' is identical to the system 10 except for the construction of the integrated unit 120, and in particular the suction regulator 24' and the external female catheter 122. The components of the system 10' which are common to the system 10 will be given the same reference numbers and the details of their construction, arrangement and operation will not be reiterated in the interest of brevity. The suction regulator 24' is identical in construction to the suction regulator 24 except that the regulated suction port 24B terminates in a tubular connector 24B'. The tubular connector 24B' is best seen in FIGS. 17 and 18 and is configured to receive the proximal end of a tubing section of the external female catheter 122 so that the regulated suction produced by the suction regulator is applied to the external female catheter. The external female catheter 122 is best seen in FIGS. 17 and 19 and basically comprises an elongated suction tube 122A and a removable liquid permeable cover 122B. The elongated suction tube 122A is best seen in FIGS. 19 and 20 and basically comprises an assembly of an elongated flexible conduit or tubing section 124, an optional cover tube 126, a multi-slot end-piece 128, and a section of malleable wire 130.

The conduit or tube 124 is a section of conventional tubing formed of any suitable flexible material, e.g., flexible PVC tubing, like used in hospitals to carry fluids via suction and has a distal end 124A and a proximal end 124B. The proximal end 124B of the tubing section 124 receives the tubular connector 24B' of the suction regulator 24' to thereby connect the elongated suction tube 122A to the suction regulator. The distal end 124A of the tubing section 124 receives the proximal end 128A of the multi-slot end-piece 128.

The removable liquid permeable cover 122B is in the form of a cylindrical sponge-like body having a rounded or domed distal end. The cover 122B will be described in detail later. Suffice it for now to state that that in one exemplary preferred embodiment of this invention the cover 122B is approximately 5.75 inches long measured from its distal end to its proximal end and has an outside diameter of approximately 1.125 inches. The cover is mounted on the distal end portion of the elongated suction tube 122A and overlies approximately the distal-most 5 inches of the elongated suction tube. In particular, the cover is mounted on and over the distal end 124A of the tubing section 124 and on and over the cover tube 126 and the multi-slot end-piece 128, with the proximal portion of the cover overlying approximately 0.5 inch of the tubing section 124 to ensure an air-tight seal.

The multi-slot end-piece 128 forms a first section of the elongated suction tube and is a flexible rod-like member, e.g., an extrusion of any suitable flexible material, e.g., polyurethane. In the exemplary embodiment shown the end-piece is approximately 5 inches long with an outside diameter of approximately 0.425 inch. The end-piece 128 has a generally circular profile in cross-section (see FIG. 21) and includes plural longitudinally extending passageways or channels 132A, 132B, 132C and 132D, which run the full length to the end-piece. The passageways are equidistantly spaced about the periphery of the end-piece and each passageway includes a narrow width, e.g., 0.1 inch, longitudinally extending slot at the surface of the periphery of the end-piece. In particular, the passageway 132A includes an associated slot 134A, the passageway 132B includes an associated slot 134B, the passageway 132C includes an associated slot 134C, and the passageway 132D includes an associated slot 134D. The proximal end of each of the passageways 134A-134D is open, as is the distal end of each of those passageways. A short length, e.g., 0.5 inch, of the proximal end of the end-piece 124 is disposed within the distal end 124A of the tubing section 124. The tubing section 124 from the proximal end of the end-piece to the connector 24B' of the suction regulator 24' forms what can be called a second section of the suction tube 122A.

The optional cover tube 126 is a section of heat shrinkable tubing, which is disposed over the portion of the end-piece 128 immediately adjacent the distal end 124A of the tubing section 124, thereby covering or closing off the underlying proximal portions of the slots 134A-134D, but leaving approximately 40 mm of the distal end portions of the slots uncovered or exposed. Thus, when the proximal end of the end-piece 128 is disposed within the distal end 124A of the tubing section 124 and the heat shrinkable cover tube 126 is in place, the regulated suction applied from the suction regulator to the tubing section 124 will be applied to the open proximal end of each of the passageways 132A-132D down the length of the passageways to exit the uncovered portions of the slots 134A-134D, respectively, and the open distal ends of those passageways.

It should be noted that while the exemplary embodiment shown and described above includes four passageways and four associated slots, it is contemplated that the end-piece can have any number of passageways, with associated slots, e.g., three passageways and three associated slots. The key feature being that the slots are directed in different, equidistantly spaced radial directions with respect to the central longitudinal axis of the end piece. As such irrespective of the orientation of the elongated external catheter about its central longitudinal axis with respect to the urethra opening of the patient, there will be at least one slot generally directed to the urethra opening to accept urine therefrom. Moreover, the distal end of each of the passageways 134A-134D is open. Thus, when the external female catheter is disposed adjacent the urethra of the patient, and regulated suction applied to it from the suction regulator, the regulated suction is applied to the distal end portion of the cover 122B, i.e., the distal portions of the slots 134A-134D that are not covered by the cover tube 126. That action draws urine from the patient through the distal portion of the cover 122B into the exposed portions of the slots 134A-134D and the open distal ends of the passageways 132A-132D and from there through those passageways into the tubing section 124 and from there through the suction regulator 24' to the collection canister 12. The use of multiple channels facilitates the removal of urine while minimizing the chance that the channels will be collapsed by portions of the patient's anatomy.

As best seen in FIGS. 18 and 21 the end-piece 128 includes a small diameter, e.g., 0.051 inch, central passageway 136 in which the malleable wire 130 is located. The malleable wire can be formed of any suitable material, e.g., stainless steel, aluminum, provided that it is biocompatible and can be readily bent into a desired shape and will hold that shape. With the wire 130 located in the passageway 136 and the cover 122B mounted on the distal portion of the elongated suction tube 122A, the end-piece 128 can be bent into a somewhat arcuate shape, so that the cover 122B conforms closely and comfortably to the anatomy of the patient contiguous with the patient's urethra opening. Other dimensions of the end-piece 128 are shown in FIG. 21.

Turning now to FIG. 18, the details of the cover 122B will now be described. In particular, as mentioned earlier the cover 122B is a cylindrical member whose distal end or tip is rounded or domed and is approximately 5.75 inch in length, and with a 1.125 inch outside diameter. The cover includes a central passageway 138 extending from its proximal end to a point closely adjacent its distal end. The inside diameter of the passageway 138 is approximately 0.375 inch. The thickness of the rounded tip is approximately 0.375 inch. The passageway 138 is configured for receipt of the end-piece 128, the optional cover tube 126, and the distal end portion of the tubing section 124. To that end the internal diameter of the central passageway of the cover 122B is slightly smaller than the external diameter of the end-piece 128 so that the cover 122B is held thereon by friction. With the cover in place, the closed distal end of the cover overlies the open distal ends of the passageways 134A-134D of the end-piece 128.

The cover is formed of a soft (e.g., somewhat compressible), liquid-permeable material, e.g., hydrophilic polyurethane foam, although it could be formed of other liquid permeable hydrophilic materials such as PVA (polyvinyl alcohol) sponge, cellulose, etc. One preferred exemplary embodiment of a hydrophilic polyurethane foam cover is a hybrid foam having a pore size of approximately 150-300 microns, and a density in the range of 16-21 grams.

As is known, hydrophilic polyurethane foam is created by mixing chemicals including water. After the foam is formed it still contains a large quantity of water, approximately 50% by weight. In many applications, polyurethane foam is provided dry. As such, polyurethane foam is often dried by heating as part of the manufacturing process.

For the female catheters of the subject invention, it is desirable to have the foam covers as hydrophilic as possible so that urine is captured effectively. The polyurethane foam is most hydrophilic when it is moist, such as is the case immediately after foam formation and without drying. As such the foam making up all of the sponge covers of this invention is not dried. Rather, it is packaged moist in a sealed package that has a very low moisture transmission rate so that it is moist at time of use. In particular commercial embodiments of this invention will be preferably packaged wet. Since it is packaged wet, the cover preferably will include an antimicrobial additive to prevent microbial growth. Any suitable commercially available anti-microbial additive can be used, e.g., isothiazolinone treatments, zinc pyrithione, thiabendazole, silver and quaternary ammonium compounds and Polyhexamethylene biguanide (PHMB) and chlorhexidine gluconate (CHG). In addition to helping with storage, the antimicrobial agent inhibits the growth of microbes during use of the system of this invention, reducing the risk of infection.

Operation of the external female catheter 120 is similar to the operation of the external female catheter 20 and is as follows. In particular, the suction regulator 24' operates in an identical manner as the suction regulator 24. Thus, when regulated suction produced by the suction regulator 24' is applied connector 24B' of the port 24B that regulated suction will be applied to the exposed distal portions of the slots 134A-134D and the contiguous open distal ends of the passageways 132A-132D, respectively, to draw any urine that the female patient voided into the cover from there into those passageways, whereupon that urine will be pulled into the interior of the tubing section 124 and carried by air from the suction regulator 24'. From there the urine is carried to the receptacle or canister 12. In particular, with the system 10' as described above when suction is applied from the hospital's suction line or wall regulator 16, that high level of suction is conveyed through the tubing section 14, from whence it is applied to the canister or receptacle 12 and the associated tubing section 18 to the line suction port 24A of the suction regulator 24, whereupon it is regulated (e.g., reduced) by operation of the suction regulator to a much lower operating level, e.g., 40 mmHg. That reduced or regulated suction will appear on the suction port 24B of the regulator 24' and from there to the external catheter 122 to thereby draw urine from the external catheter 122 back through the regulator 24', and out through the tubing section 18 into the receptacle or canister 12 for collection therein.

One of the key features of the integral suction regulator and female catheter 120 allows, like the features of the integral suction regulator and female catheter 20, is that it can be used in a system like 10' to be attached to line suction. This configuration allows for far greater airflow than conventional methods, which aids in urine capture and drying of the catheter. Moreover, the openings through which the regulated suction is applied to the cover 120B is somewhat confined in that only approximately 40 mm of the slots 134A-134D are exposed to provide suction to the contiguous portions of the cover 122B. By decreasing the opening size of the extrusion, i.e., the exposed slots, the subject invention is able to concentrate the same amount of airflow, increasing the velocity of the air to compound the benefits of the high volume of airflow provided by the regulator. However, since the foam component is absorbent regardless of location, over-concentration of the airflow results in location-dependent capture and non-uniform drying and may leave the patient wet or result in leaks. Iterative bench-top testing has suggested providing open slots of approximately 40 mm/1.5 inch results in optimal performance, as defined by the maximum capturable urination rate before the system is overwhelmed and leaks.

As should be appreciated by those skilled in the art, when the tubing in an external catheter circuit becomes filled with urine, either due to a patient urinating a large volume at once, or a temporary occlusion along the circuit, air entrainment is no longer possible, and urine must be pulled through the tubing by the force of suction alone. In this scenario, for any section of tubing traveling along a vertical incline, gravity opposes the suction force limiting the height of any vertical incline which can be overcome. Forty mm of Hg is equivalent to the pressure exerted by approximately 21 inches of water, meaning that for any suction-based urine management system operating at 40 mm Hg no part of the system can have a vertical incline greater than 21 inches without risking failure if the external catheter circuit becomes filled with urine. Conventional external catheter systems, (which may have a tubing path of up to 20 feet between the wall regulator and the patient) present a significant possibility that some portion of the tubing path may have a 21 inch incline, so that such prior art systems are prone to that type of failure if the external catheter circuit becomes filled with urine. In contradistinction, the systems of this invention make use of tubing that is only approximately 6 inches to approximately 24 inches between the regulator and patient's urethra opening. This means that the integrated suction regulators/external catheters of the subject invention should not be prone to failure due to too much urine.

It must be pointed out at this juncture that the various components of the integrated unit 20 and 120 shown and described above are merely exemplary of various components that may be used in accordance with this invention to provide the capabilities as discussed above. Thus, various changes can be made to the integrated external female catheter and suction regulator of subject invention from the exemplary embodiments described above. For example, the use of the optional cover tube 126 can be omitted. In such a case the distal end 124A of the tubing section 124 should extend to approximately 40 mm from the distal end of the end-piece 128, whereupon the tubing section 124 itself closes off the slots in the passageways up to the last (distal) 40 mm of the end-piece. The use of the optional heat shrinkable tube section 126 is a preferred means for covering portions of the slots proximally of the distal-most 40 mm thereof, since heat shrinkable tubing is more economical than the material making up the tubing section 124. Moreover, the end-piece 124, itself, can be constructed so that the slots 134A-134D do not extend the entire length of the associated passageways 132A-132D, but only the distal-most 40 mm thereof. Thus, it is contemplated that the end-piece can be constructed so that only the distal-most portion, e.g., approximately 40 mm, of the passageways 132-132D include slots 134A-134D, so long as the remaining portion of the passageways are configured to carry suction therethrough without leakage and so long as the entire length of the end-piece along which the cover 122B extends is malleable to be conformable to the anatomy of the patient.

Moreover, the suction regulators 24 and 24' may be constructed somewhat similarly to the suction controller 300 shown in FIGS. 9A and 10A of U.S. application Ser. No. 14/227,587 entitled the Gastric Sizing Systems Including Instruments And Methods Of Bariatric Surgery filed on filed on Mar. 27, 2014, now U.S. Pat. No. 10,646,625, which is assigned to the same assignee as this invention and whose disclosure is specifically incorporated by reference herein. That suction controller if used in an integrated unit 20 or 120 like the subject invention would be modified to omit the disk 314 and thus result in a cost saving. In the invention of that patent the disk 314 is provided to seal off the system when positive pressure is applied for leak testing. The integrated unit 20 of this invention and any other integrated units constructed in accordance with this invention will never exceed atmospheric pressure, so a disk 314 is unnecessary. Moreover, the suction controller 300 of that patent if used in an integrated unit like that of this invention will need to be sized and configured to produce the desired regulated suction value.

Various other changes can be made to systems of this invention, in addition to changes in the suction regulator 24 and 24'. For example, some hospitals in which the subject integrated unit will be used have special regulator set-ups that allow for connection of a suction canister directly below the wall regulator. In such a case the tubing section 14 of the system 10 may be omitted. Also, it should be pointed out that the integrated units of this invention are not limited to use in hospitals, but can be used in any application providing care to a patient.

Figure 38:
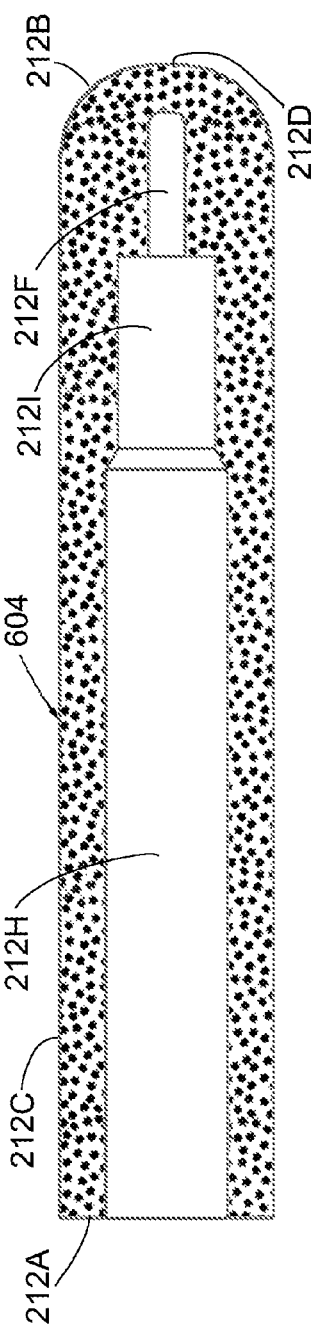
FIG. 38 is a sectional view, like that of FIG. 37, but showing an alternative sponge cover that can be used in the external catheter of FIG. 34.

For some applications, e.g., where the medical or other facility in which the female patient is located has its own source of suction which is in the desired range for use with a female external catheter, the integrated external female catheter and suction regulator devices as shown in FIGS. 1-21 can be replaced by an external female catheter without an suction regulator. Thus, various external female catheters without a suction regulator integrated with the catheters are contemplated by this invention. For example, FIGS. 22-29 show one such exemplary embodiment of an external female catheter 200 constructed in accordance with this invention, FIGS. 30-31 show another exemplary embodiment of an external female catheter 300 constructed in accordance with this invention, FIGS. 32-33 show still another exemplary embodiment of an external female catheter 400 constructed in accordance with this invention, FIGS. 34-37 show yet another exemplary embodiment of an external female catheter 500 constructed in accordance with this invention, and FIG. 38 shows an alternative cover that can be used in the external female catheter 500 in lieu of the cover that is shown in FIGS. 34-37.

Each of those exemplary alternative external female catheters will be described in detail hereinafter. Suffice it for now to state that each includes an elongated suction tube having a distal end portion which is enclosed within a liquid pervious cover formed of a sponge material, with the proximal end of the suction tube being configured to be coupled to a source of suction which is in the desired operating range. If desired a receptacle or canister, like that described above, can be coupled to the external female catheter to collect the urine from the external female catheter.

Turning now to FIGS. 22-29, it can be seen that the external female catheter 200 basically comprises an elongated suction tube 202 and a cover 204. The elongated suction tube 202 is itself made up of several components, to be described shortly, and has a longitudinal central axis X, a distal end 206, a proximal end 208, and at least a first passageway 210 (FIG. 23) extending longitudinally therethrough from the distal end to the proximal end. The proximal end is configured to be coupled to any suitable source of suction that provides suction at a value or level of 40-200 mmHg, and most preferably at 125 mmHg. The distal end 206 of the suction tube 202 is open as will be appreciated from the discussion to follow.

The cover 204 is similar in many respects to the covers disclosed in the above described embodiments and is formed of a body of a soft, moist hydrophilic, e.g., polyurethane, foam. The cover has a length in the range of 4 inches to 8 inches, a longitudinal axis X and an external surface 212. The external surface 212 comprises a proximal end surface 212A, a distal end surface 212B, and an arcuate lateral surface 212C interposed between the proximal end surface and the distal end surface. The proximal end surface is planar, but can be arcuate or some other shape if desired. The distal end surface 212B is preferably arcuate, e.g., dome shaped, but can be planar if desired. If dome shaped it has an apex 212D. If planar the entire planar surface forms the apex of the distal end surface. In any case, the entire exterior surface, including the arcuate lateral surface, is uncovered so that it is completely exposed. Therefore, since the cover is formed of a body of hydrophilic foam the entire arcuate lateral surface is fluid-permeable and extends around the longitudinal axis X from the distal end surface to the proximal end surface.

The cover 204 includes a central cylindrical bore 212E having an inside diameter of 0.42 inch centered on the central longitudinal axis X of the cover and extending from the proximal end surface 212A of the cover to a point closely adjacent the apex 212D. The bore 212E is configured to frictionally receive the elongated suction tube 202 therein, whereupon the portion or section of the elongated suction tube contiguous with the distal end 206 is enclosed within the body of the cover. That action is accomplished by inserting the distal end 206 of the suction tube into the open proximal end of the bore 212E at the proximal end of the cover 204 and moving the suction tube and cover with respect to each other until the distal end of the suction tube reaches the distal end of the bore. Once the elongated suction tube 202 is in its desired position within that the cover 204 it will be held in place by frictional engagement with the inner surface of the contiguous bore 212E so that the cover will be resistant to accidental displacement on the elongated suction tube.

In accordance with one preferred embodiment of this invention the distal end of the bore 212E (and hence the open distal end 206 of the elongated suction tube) is spaced by a distance within the range of 0.125 inch to 0.375 inch from the apex 212D of the cover, with the open distal end of each of the passageways 132A-132D of the suction tube being preferably located 0.25 inch from the apex 212D of the cover.

The elongated suction tube 202 basically comprises four components, namely, a flexible tube section 214, a tubular coupler 216, a heat shrink tube 218, and an elongated extrusion 220 having at least one longitudinally extending passageway and at least one associated longitudinally extending slot. The elongated extrusion 220 is constructed similarly to the extrusion 128 described above. Hence in the interest of brevity the common features of the extrusion 220 will be given the same reference numbers as the extrusion 128 and the details and operation of those features will not be reiterated. Suffice it for now to state that the heretofore identified at least one passageway 210 constitutes one of the passageways 132A, 132B, 132C, or 132D of the extrusion 220.

Figure 26:
FIG. 26 is an isometric view of another one of the components, i.e., a flexible suction tube, forming a portion of the external catheter shown in FIGS. 22 and 23.
Figure 29:
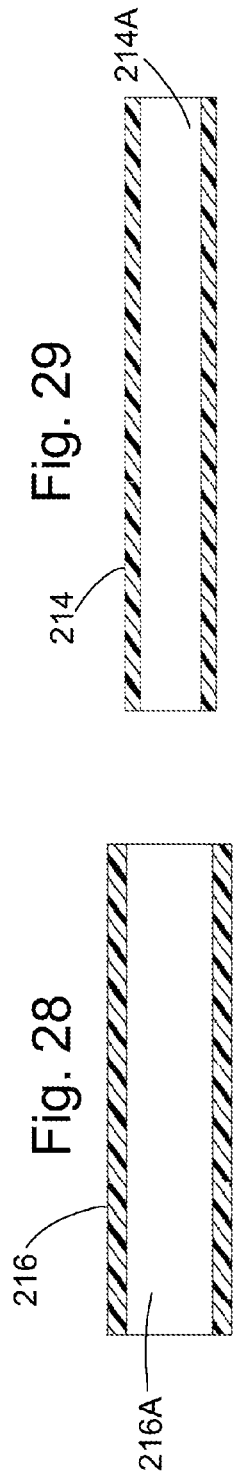
FIG. 29 is a sectional view taken along line 29-29 of FIG. 26.
Figure 30:
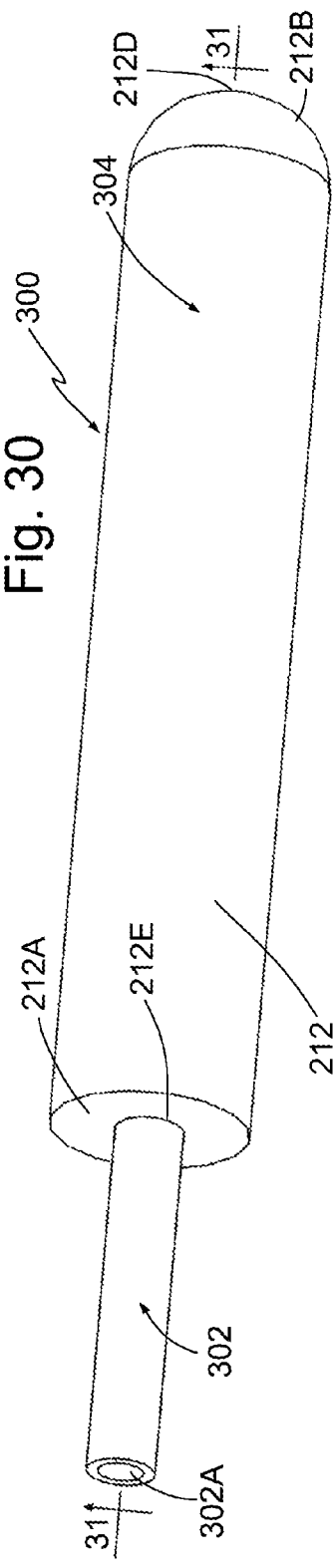
FIG. 30 is an isometric view of another exemplary external catheter constructed in accordance with the second aspect of this invention, wherein the external catheter is not part of an integrated system including an integrated suction regulator such that it can be used by itself with any appropriate source of suction and, if desired, any receptacle or canister for collecting urine from the female patient.

The flexible tube section 214, is best seen in FIGS. 23, 26 and 29, has a length, e.g., 2.5 inch and is formed of conventional flexible tubing, e.g., polyvinylchloride (PVC) tubing. The tube section if preferably transparent, but may be translucent or opaque, as desired. The tube section 214 has an outside diameter of 0.375 inch, and a central passageway 214A having an inside diameter of 0.25 inch. The central passageway 214A extends through the entire length of the tube section from its distal end to its proximal end.

Figure 25:
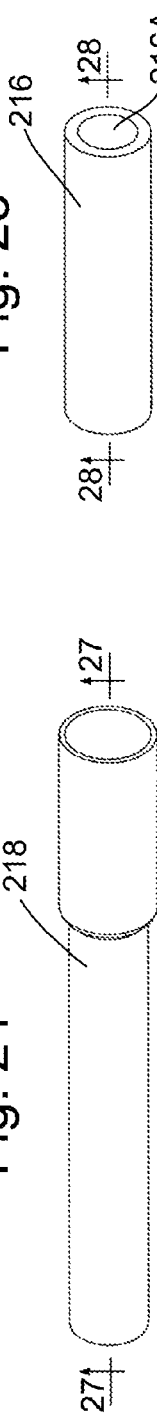
FIG. 25 is an isometric view of another one of the components, i.e., a short tube section, forming a portion of the external catheter shown in FIGS. 22 and 23.
Figure 28:
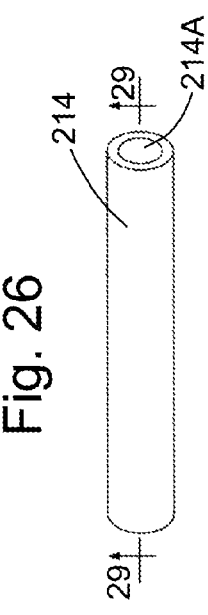
FIG. 28 is a sectional view taken along line 28-28 of FIG. 25.

The tubular coupler 216, is best seen in FIGS. 23, 25 and 28, and is in the form of a short length, e.g., 2 inches, of flexible tubing, having an outside diameter of 0.5 inch, and a central passageway 216A of an inside diameter of 0.35 inch. The central passageway extends through the entire length of the tubular coupler from its distal end to its proximal end. The tubular coupler 214 is formed of any suitable material, e.g., PVC and is preferably transparent, but can be translucent or opaque. The distal end of the flexible tube 214 is disposed and fixedly secured within the proximal end of the passageway 216A of the tubular coupler 216 by cyclohexanone or some other suitable adhesive. The proximal end of the elongated extrusion 220 is located within the distal end of the passageway 216A of the tubular coupler.

Figure 27:
FIG. 27 is a sectional view taken along line 27-27 of FIG. 24.

The heat shrink tube 218, is best seen in FIGS. 24 and 27, and is a tubular member formed of any suitable heat shrinkable material, e.g., adhesive lined polyolefin. The heat shrink tube is of a length of within the range of 2 inches to 4 inches and is disposed and shrunk about a distal portion of the outer surface of the tubular coupler 216 and a proximal and contiguous portion of the elongated extrusion 220 to fixedly secure those three components together and thus form the elongated suction tube 202. As can be best seen in FIG. 23 the distal end of the heat shrink tube 218 terminates a distance of between 0.5 inch and 2.5 inches from the distal end of the elongated extrusion 220. Accordingly the slots 134A, 134B, 134C and 134D will be open from the distal end of the extrusion to a point between 0.5 inch and 2.5 inches from the distal end, with the remainder of those slots being closed or sealed off by the heat shrink tube to form a configuration similar to that shown in FIG. 19.

The cover 204 is configured for external disposition with respect to the female such any portion of the liquid-permeable arcuate lateral surface will be in fluid communication with the urethra opening of the female so that urine voided by the female passes into the at least a first passageway to be carried by suction therefrom out of the external catheter for collection. In particular, and in accordance with one preferred method of the use of the external female catheter 200 (as well as the external female catheters 300, 400 and 500, and any other external female catheter constructed in accordance with this invention) the catheter is designed so that it is oriented generally vertically between the female's legs with the distal end of the cover facing downward and so that the female's urethra opening is immediately adjacent, and preferable in contact with, a middle portion of the arcuate lateral surface 212C whether the female is supine or prone. Since the entire periphery of the arcuate lateral surface is liquid permeable, the external catheter 200 can be oriented so that any portion of the periphery of the cover 204 at approximately the middle thereof can be disposed immediately adjacent and preferably in contact with the female's urethra opening. In that state urine voided by the female will enter that peripheral portion of the cover, and under the influence of gravity and the suction provided by the elongated suction tube will flow downward through the body of the cover into the elongated suction tube, from whence it will be carried for collection, and with little or no urine leakage out of the female catheter. Specifically, urine voided by the female will enter into whichever of the uncovered slots 134A-134D is facing towards the female's urethra opening, and from there the urine will be carried downward by the air flow engendered by the suction into the associated passageway 132A-132D, as the case may be. In addition, any urine which reaches the domed end of the cover will flow into the distal ends of the passageways 132A-132D since those ends are open. The urine entering the passageways will be carried through the passageways into the central passageway 216A of the tubular coupler 214, from whence it will be carried into and through the central passageway 214A of the flexible tubing section 216. From there the urine will carried away for collection. That urine collection action may be accomplished by connecting a receptacle or canister 12 to the proximal end of the elongated suction tube 202 via any type of conduit and associated coupler (not shown).

In the interests of comfort and fit, at least the portion of suction tube which is enclosed within the cover is preferably malleable, so that it and the enclosing cover can be bent to conform to the female's anatomy. Accordingly, the external catheter 200 includes a malleable wire, like the wire 130 described above. The malleable wire 130 extends down the central passageway 136 of the elongated extrusion 220. In the interest of brevity the details of the construction and operation of the malleable wire 130 will not be reiterated. It should be noted that while it is preferred that the portion of the external catheter encompassed by the cover be malleable, that configuration is not mandatory.

Turning now to FIGS. 30 and 31, the external female catheter embodiment 300 will now be described. It basically comprises an elongated suction tube 302 and a liquid permeable cover 304. That external female catheter 300 is considerably simpler in construction than the embodiment 200 insofar as its elongated suction tube is concerned. In particular, the elongated suction tube 302 of the external female catheter 300 is a single unitary component, i.e., a length of flexible tubing. The flexible tubing is formed of any suitable material, e.g., PVC.

The cover 304 of the external female catheter 300 is the same basic construction as the cover of the external female catheter 200. Hence the common features of the cover 304 will be given the same reference numbers as those of the cover 204, and the details of their construction and operation will not be reiterated in the interest of brevity.

The elongated suction tube 302 has a length within the range of 4 inch to 8 inches, an outside diameter of 0.375 inch, and a central passageway 302A extending the entire length of the suction tube 302 from its distal end 302B to its proximal end 302C. The inside diameter of the central passageway is 0.25 inch.

The distal end and contiguous portion of the suction tube 302 is extended into and frictionally held within the cylindrical bore 212E of the cover 204 so that the cover is resistant to accidental displacement with respect to the suction tube. That action is accomplished by inserting the distal end 302B of the suction tube into the open proximal end of the bore 212E at the proximal end of the cover 304 and moving the suction tube and cover with respect to each other until the distal end of the suction tube reaches the distal end of the bore. Once the elongated suction tube 302 is in its desired position within that the cover 304 it will be held in place by frictional engagement with the inner surface of the contiguous bore 212E so that the cover will be resistant to accidental displacement on the elongated suction tube. When so located the distal end 302B of the suction tube 302, which is open, will be spaced by a distance in the range of 0.125 inch to 2 inches from the apex 212D of the cover 304, with the most preferably distance being 1.5 inches.

The use of the external female catheter 300 is similar to the use of the external female catheter 200. In particular, the external female catheter 300 is disposed with respect to the female in the same manner as that of the external female catheter 200. Accordingly, when the female voids, the urine exiting her urethra will enter that peripheral portion of the cover 204, and under the influence of gravity and the suction at the level of 40-200 mmHg provided by the elongated suction tube will flow down the interior of the sponge body making up the cover into the open distal end 302B of the elongated suction tube 302, from whence it will be carried through the central passageway 302A and out its open proximal end 302C for collection. That urine collection action may be accomplished by connecting a receptacle or canister 12 to the proximal end of the elongated suction tube 302 via any type of conduit and associated coupler (not shown). As is the case with the external catheter 200, use of the external catheter 300 will result in little or no urine leakage out of the female catheter.

In the interest of simplicity of construction and cost the external female catheter 300 does not make use of a malleable wire to provide the catheter with the ability to be conformed to the anatomy of the female user. The external female catheter 400 makes up for the lack of malleability of the external female catheter 300, by providing that feature, but still with a construction that is simpler than that of the external female catheter 200. Thus, attention is now directed to FIGS. 32 and 33 wherein the details of the construction and operation of the external female catheter 400 will now be described.

The external female catheter 400 basically comprises an elongated suction tube 402, a cover 404, and a malleable wire. The cover 404 of the external female catheter 400 is of similar construction to the cover 204 of the external female catheter 200. Hence the features of the cover 404 that are common with the features of the cover 204 will be given the same reference numbers and the details of their construction and operation will not be reiterated in the interest of brevity. The cover 404 does have a difference from the cover 204 of the external female catheter 200. In particular, it includes a cylindrical cavity 212F located immediately distally of the bore 212E. The cylindrical cavity 212F is of smaller inside diameter, e.g., 0.25 inch, than the inside diameter of the bore 212E. The cylindrical cavity 212F is configured to facilitate the passage of urine into the open distal end of the suction tube 402, as will be described shortly. The malleable wire of the external female catheter 400 is the same construction as the malleable wire of the embodiment 200. Hence it will be given the same reference number, i.e., 130, and the details of its construction and operation will not be reiterated in the interest of brevity.

The elongated suction tube 402 is an elongated flexible tube formed of any suitable material, e.g., thermoplastic elastomer, having a length with the range of 4 inches to 8 inches. It includes a passageway 402A extending the length of the suction tube parallel to, but slightly laterally offset from, its central longitudinal axis X. The passageway 402A extends from the distal end 402B of the suction tube to its proximal end 402C. The inside diameter of the passageway 402A is 0.2 inch. The outside diameter of the suction tube 402 is 0.375 inch. The suction tube 402 includes a second passageway 402D extending down the length of the suction tube from its distal end 402B to its proximal end 402C. The second passageway 402D is laterally offset from the passageway 402A. The inside diameter of the second passageway 402D is 0.062 inch and is configured to closely hold the malleable wire 130 therein as shown in FIG. 33.

The distal end 402 and contiguous portion of the suction tube 402 is disposed and frictionally held within the cylindrical bore 212E of the cover 404 so that the cover is resistant to accidental displacement with respect to the suction tube. That action is accomplished by inserting the distal end 402B of the suction tube into the open proximal end of the bore 212E at the proximal end of the cover 404 and moving the suction tube and cover with respect to each other until the distal end of the suction tube reaches the distal end of the bore. Once the elongated suction tube 402 is in its desired position within that the cover 404 it will be held in place by frictional engagement with the inner surface of the contiguous bore 212E so that the cover will be resistant to accidental displacement on the elongated suction tube.

The use of the external female catheter 400 is similar to the use of the external female catheter 300 except that being malleable by virtue of the inclusion of the malleable wire, it can be conformed to the anatomy of the female before it is operated. In particular, the external female catheter 400 is disposed with respect to the female in the same manner as that of the external female catheter 300, except for being bent to a shape conforming to the female's anatomy before suction is applied. Accordingly, after the catheter 400 has been bent and disposed between the female's legs adjacent the female's urethra opening as described above, when the female voids, the urine exiting her urethra will enter that peripheral portion 212C of the cover 404, and under the influence of gravity and the suction provided by the elongated suction tube will flow down the interior of the sponge body making up the cover into the cavity 212F at the open distal end 402B of the elongated suction tube 402. The inclusion of the cavity 212 serves to increase the internal surface area of the foam material making up the cover at the distal end 402B of the suction tube 402. For example, in FIG. 31 the surface area of foam at the distal end 302B of the suction tube 302 is smaller, and even though the foam is permeable, this reduces the liquid flow capacity of the external catheter 300. In contrast, and due to presence of the cavity 212F of the external catheter 400, the surface area of foam at the distal end 402B of the suction tube 402 is much greater, thereby providing increased overall urine flow capacity. The surface area of the cavity 212 beyond the distal end of the suction tube should be at least twice the cross-sectional area of the inside of the passageway 402A. More preferably, it should be five times that cross-sectional area, and most preferably, ten times that cross-sectional area. Once the urine enters into the open distal end 402B of the suction to it will be carried into and through the passageway 402A and out its open proximal end 402C for collection. That urine collection action may be accomplished by connecting a receptacle or canister 12 to the proximal end of the elongated suction tube 402 via any type of conduit and associated coupler (not shown). As is the case with the external catheters 200 and 300, use of the external female catheter 400 will result in little or no urine leakage out of that catheter.

Figure 36:
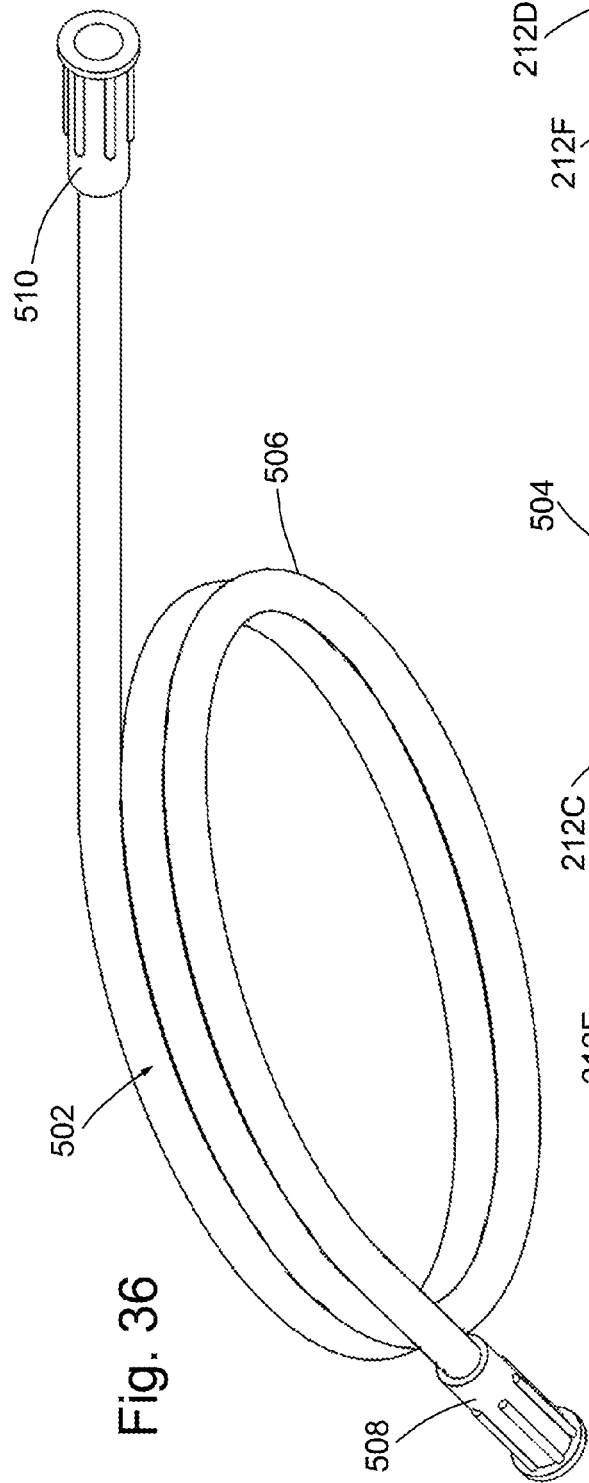
FIG. 36 is an enlarged isometric view of one component, e.g., a suction tube, forming a portion of the external catheter of FIG. 34.
Figure 37:
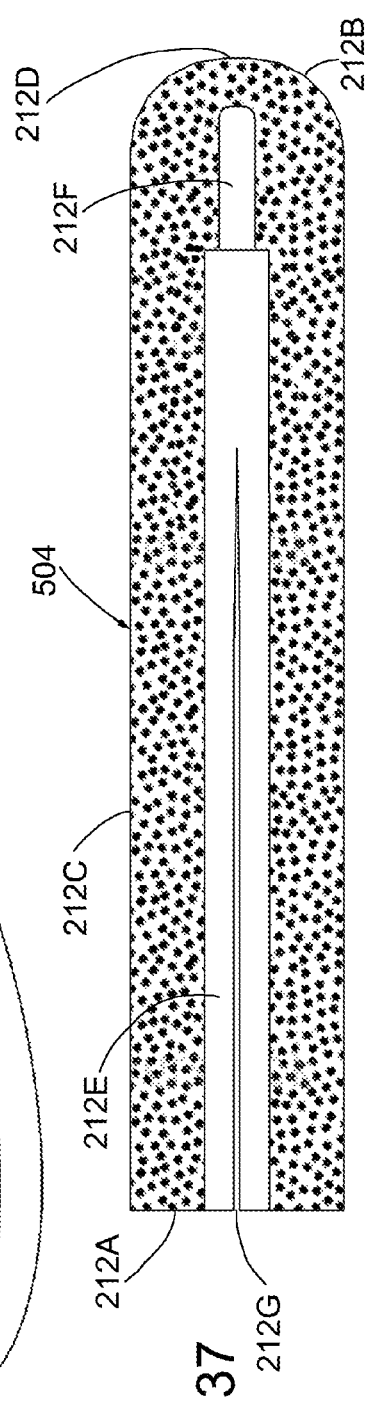
FIG. 37 is a sectional view, taken along a plane perpendicular to the plane of the sectional view of FIG. 35, but showing only one component, i.e., a sponge cover, of the external catheter of FIG. 34.

Turning now to FIGS. 34-37 the details of the construction and operation of the external female catheter 500 will now be described. The external female catheter 500 basically comprises an elongated suction tube 502 and a cover 504. The elongated suction tube 502 is best seen in FIG. 36 and basically comprises a length, e.g., 72 inches, of flexible tubing 506 having a central passageway 506A (FIG. 35) extending through the entire length of the flexible tube from its distal end to its proximal end. The inside diameter of the central passageway 506A is 0.25 inch. The outside diameter of the flexible tube 506 is 0.375 inch. A first tubular coupler 508 is secured to the proximal end of the flexible tube 506. A second tubular coupler 510 is secured to the distal end of the flexible tube 506. Each tubular coupler is of conventional construction like that used in the medical field to couple various medical components together by interposed tubing so that liquid or other fluids can be transported between those components. Thus, each tubular coupler has a central passageway extending through its entire length. For example, as can be seen in FIG. 35, the tubular coupler includes a central passageway 510A. The tubular coupler 510 and its contiguous portion of the flexible tubing 506 is configured to be disposed and frictionally held within a cylindrical bore in the cover 504 as will be described shortly.

The cover 504 is similar in construction to the cover 404 of the external female catheter 400. Hence the features of the cover 504 which are common with the features of cover 404 will be given the same reference numbers and the details of their construction and operation will not be reiterated in the interest of brevity. The cover 504 does differ from the cover 504 in that the cover 504 includes a longitudinally extending slit 212G. The slit 212G is a planar radially extending cut that extends linearly from the proximal end 212A of the cover towards the distal end of the cover, with the distal end of the slit terminating approximately 0.5 inch to approximately 3 inches from the distal end of the cover. In the exemplary embodiment shown the distal end of the slit terminates approximately 3 inches from the cover. The slit 212G is in communication with the bore 212E to facilitate insertion of the distal end portion of the suction tube 402 into the bore of the cover 404. In particular, it provides access through the cover which the tubular coupler 510 and the contiguous portion of the flexible tube 506 can be inserted laterally, instead of being inserted longitudinally through the open end of the bore 212E at the proximal end 212A of the cover as is the case of the external female catheters 200, 300 and 400. Once laterally inserted through the slit the distal end portion of the suction tube can be moved with respect to the cover along the longitudinal axis X until the tubular coupler 510 is located within the distal end portion of the bore 212E (its desired position). The slit 212G enables the user to visualize the position of the tubular coupler with respect to the cover so that it will be at that desired position for securement thereat. In this regard, when the suction tube 502 is that desired position within that the cover 504 it will be held in place by frictional engagement of the inner surface of the bore 212E with the exterior surface of the flexible tube 506, and by the frictional engagement of the inner surface of the bore 212 with the exterior surface of the tubular coupler 510.

The use of the external female catheter 500 is similar to the use of the external female catheter 300. In particular, the external female catheter 500 is disposed with respect to the female in the same manner as that of the external female catheter 300. Thus, after the catheter 500 has been placed between the female's legs adjacent the female's urethra opening as described above, when the female voids, the urine exiting her urethra will enter that peripheral portion of the cover 502, and under the influence of gravity and the suction provided by the elongated suction tube will flow down the interior of the sponge body making up the cover 504 into the open distal end of the passageway 510A in the tubular coupler 510, from whence it will be carried through the central passageway 506A of the flexible tube 506. From there the urine will be carried through the central passageway of the tubular coupler 508 at the proximal end of the suction tube for collection. That urine collection action may be accomplished by connecting a receptacle or canister 12 to the tubular coupler 508 via any type of conduit or tube inserted into the open proximal end of the passageway in the tubular coupler 508. As is the case with the external catheters 200 and 300, use of the external female catheter 400 will result in little or no urine leakage out of that catheter.

Turning now to FIG. 38 there is shown an alternative cover 604 that can be used in the external female catheter 500 in lieu of the cover 504. The cover 604 is similar in most respects to the cover 504 and hence its common features will be given the same reference numbers as the features of the cover 504. Moreover, the details of the construction and operation of those common features will not be reiterated in the interest of brevity. The cover 604 is designed so that the distal portion of the suction tube 502 can be readily introduced into the cover axially from the open proximal end of the central bore. To that end, the cover 604 does not need to, and does not, include the longitudinally extending slit 212G, which facilitates lateral entry. Rather, the central bore of the cover 604 is of a larger internal diameter than the central bore 212E of the cover 504 so that the distal end portion of the suction tube 502 and its contiguous flexible tube 506 can be inserted axially into the open proximal end of the central bore until it is fully within the cover, like shown in FIG. 35. In particular, the central bore of the alternative cover 604 includes bore section 212H which is located contiguous with the proximal end 212A of the cover 604, and a bore section 212I which is located contiguous with and distally of the bore section 212H. The bore section 212H has an inside diameter of within the range of 0.6 inch to 0.875 inch, with a preferred inside diameter of 0.7 inch. The inner diameter of the bore section 212H should be larger than the largest outer diameter of the tubular coupler 510, and the inner diameter of the bore section 212I should be smaller than the outer diameter of that tubular coupler. The bore section 212I has an internal diameter in the range of 0.375 inch to 0.55 inch, with a preferred internal diameter of 0.45 inch. The bore section is configured to frictionally receive and hold the tubular coupler 510 therein. In particular, the tubular coupler 510 and its contiguous portion of the flexible tube 506 is inserted into the open proximal end of the cylindrical bore section 212H at the proximal end of the cover 604, whereupon the suction tube 502 and cover 604 are moved with respect to each other until the distal end of the tubular coupler 510 reaches the distal end of the bore section 212I. Once the suction tube 502 is in that position it will be held in place by frictional engagement of the outer surface of the tubular coupler with the inner surface of the bore section 212I.

The use of the external female catheter 500 with the alternative cover 604 is identical with the use of the female catheter 500 having the cover 504. Thus, that method of use will not be reiterated in the interest of brevity.

As should be appreciated by those skilled in the art, the fact that each of the covers of the various external catheters of this invention is fluid-permeable throughout its entirety has a distinct advantage, namely, that the particular orientation of the cover about its longitudinal axis is irrelevant. The reason is simple, namely, any portion of the cover which would wind up confronting the urethra opening of the female when the cover is in place is fluid-permeable to readily accept the urine voided by the female. Thus, the particular orientation of the cover about its central longitudinal axis is irrelevant so long as it is fluid permeable through-out its entirety and its arcuate exterior surface is completely fluid permeable over its entirety. There are other reasons why having minimal to no impermeable surfaces is advantageous. For example, an external female catheter that is half impermeable and half permeable (longitudinally) could get suctioned to the patient resulting in injury. Because of this risk, it is desirable to use less suction to minimize the chance of injury, but this could result in increased leakage of urine. Using external catheters constructed in accordance with this invention it is recommended that vacuum regulators be set to 125 mmHg, since the completely permeable cover of the subject invention will preclude this level of suction from being fully applied to the female user. Some prior art external catheters have distal ends that are impermeable. Because the distal end of the covers of the subject external female catheters of this invention are permeable, the external female catheters of this invention have the advantage that if their distal end contacts the surface on which the female user is laying they can wick up urine that might have dripped onto the surface.

It must be pointed out at this juncture that the various components of the external female catheters 200, 300, 400 and 500 as shown and described above are merely exemplary of various components that may be used in accordance with this invention to provide the capabilities as discussed above. Thus, various changes can be made to the those female catheters from the exemplary embodiments described above. Moreover, their method of use may be different than that described above, depending upon conditions and the desires of the medical or other personnel attending the female.

Without further elaboration the foregoing will so fully illustrate our invention that others may, by applying current or future knowledge, adopt the same for use under various conditions of service.

We claim:

1. An external catheter configured to be coupled to a source of suction for removing by suction urine voided by a female, said external catheter comprising:

an elongated suction tube having a longitudinal central axis, a distal end, a proximal end, and at least a first passageway extending longitudinally therethrough from said distal end to said proximal end, said proximal end being configured to be coupled to the source of suction, said distal end being open, wherein said elongated suction tube comprises at least one continuous elongated slot extending longitudinally along said at least one first passageway for a length in the range of one inch to two inches from said open distal end, said at least one continuous elongated slot being in fluid communication with said at least one first passageway along an entire length of said at least one continuous slot, wherein said least one continuous elongated slot and said at least one first passageway comprises an extrusion, and wherein said elongated suction tube additionally comprises a coupling tube having a distal portion into which a proximal end portion of said extrusion extends, and a heat shrink tube disposed over said distal portion of said coupling tube and over said extrusion but leaving a length of said at least one slot contiguous with said open distal end of said elongated suction tube uncovered and in direct fluid communication with a cover; and wherein said cover is formed of a body of moist hydrophilic polyurethane foam, said cover having a longitudinal axis and an external surface, said external surface comprising a proximal end surface, a distal end surface and an arcuate lateral surface interposed between said proximal end surface and said distal end surface, said distal end surface having an apex, said entire body being liquid-permeable, whereupon said arcuate lateral surface is liquid-permeable and extends around said longitudinal axis from said distal end surface to said proximal end surface, said cover being directly disposed over and about said elongated suction tube to enclose a section of said elongated suction tube contiguous with said open distal end thereof, said open distal end of said elongated suction tube being spaced from said apex, said at least one continuous slot being in direct fluid communication with said cover along an entire length of said at least one continuous slot, said cover being configured for external disposition with respect to the female, whereupon any portion of said liquid-permeable arcuate lateral surface is in fluid communication with a urethra opening of the female and with said cover being oriented so that said longitudinal axis of said cover is in a generally vertical orientation with said distal end surface being pointed downward, whereupon when said external catheter is coupled to the source of suction, suction is applied down said at least one first passageway and through said at least one slot so that urine voided by the female passes through a portion of said lateral surface and flows downward through said body of said cover into said at least a first passageway to be carried by suction from said at least a first passageway out of said external catheter for collection.

2. An external catheter configured to be coupled to a source of suction for removing by suction urine voided by a female, said external catheter comprising:

an elongated suction tube having a longitudinal central axis, a distal end, a proximal end, and at least a first passageway extending longitudinally therethrough from said distal end to said proximal end, said proximal end being configured to be coupled to the source of suction, said distal end being open, said elongated suction tube comprising a tubular coupler having a central passageway and a flexible tube having a central passageway, said tubular coupler having a distal end and a proximal end in which a distal end of said flexible tube is fixedly secured, said distal end of said tubular coupler forming said open distal end of said suction tube; and a cover formed of a body of moist hydrophilic polyurethane foam, said cover having a longitudinal central axis, an external surface, a bore extending along said longitudinal central axis from said proximal end surface, and a slit extending from said proximal end of said cover to a point adjacent the proximal end of said tubular coupler and in communication with said bore, said slit providing access through which said tubular coupler and said contiguous portion of said flexible tube is inserted laterally, said external surface comprising a proximal end surface, a distal end surface and an arcuate lateral surface interposed between said proximal end surface and said distal end surface, said distal end surface having an apex, said entire body being liquid-permeable, whereupon said arcuate lateral surface is liquid-permeable and extends around said longitudinal axis from said distal end surface to said proximal end surface, said cover being directly disposed over and about said elongated suction tube to enclose a section of said elongated suction tube contiguous with said open distal end thereof, said open distal end of said elongated suction tube being spaced from said apex, said cover being configured for external disposition with respect to the female, whereupon any portion of said liquid-permeable arcuate lateral surface is in fluid communication with a urethra opening of the female and with said cover being oriented so that said longitudinal axis of said cover is in a generally vertical orientation with said distal end surface being pointed downward so that urine voided by the female passes through a portion of said lateral surface and flows downward through said body of said cover into said at least a first passageway to be carried by suction from said at least a first passageway out of said external catheter for collection, wherein said distal end of said tubular coupler is spaced by a distance in the range of 1 inch to 2 inch from said apex, and wherein said cover includes a hollow cavity extending along said longitudinal central axis from said open distal end of said elongated suction tube to a point in the range of 0.375 inch to 1 inch from said apex.

3. An external catheter configured to be coupled to a source of suction for removing by suction urine voided by a female, said external catheter comprising:

an elongated suction tube having a longitudinal central axis, a distal end, a proximal end, and at least a first passageway extending longitudinally therethrough from said distal end to said proximal end, said proximal end being configured to be coupled to the source of suction, said distal end being open, said elongated suction tube comprising a tubular coupler having a central passageway and a flexible tube having a central passageway, said tubular coupler having a distal end and a proximal end in which a distal end of said flexible tube is fixedly secured, said distal end of said tubular coupler forming said open distal end of said suction tube; and a cover formed of a body of moist hydrophilic polyurethane foam, said cover having a longitudinal axis and an external surface, said external surface comprising a proximal end surface, a distal end surface and an arcuate lateral surface interposed between said proximal end surface and said distal end surface, said distal end surface having an apex, said entire body being liquid-permeable, whereupon said arcuate lateral surface is liquid-permeable and extends around said longitudinal axis from said distal end surface to said proximal end surface, said cover being directly disposed over and about said elongated suction tube to enclose a section of said elongated suction tube contiguous with said open distal end thereof, said open distal end of said elongated suction tube being spaced from said apex, said cover being configured for external disposition with respect to the female, whereupon any portion of said liquid-permeable arcuate lateral surface is in fluid communication with a urethra opening of the female and with said cover being oriented so that said longitudinal axis of said cover is in a generally vertical orientation with said distal end surface being pointed downward so that urine voided by the female passes through a portion of said lateral surface and flows downward through said body of said cover into said at least a first passageway to be carried by suction from said at least a first passageway out of said external catheter for collection, wherein said cover includes a first bore section extending from said proximal end surface of said cover to a first intermediate point, and a second bore section extending distally from said first bore section, said tubular coupler being located in said second bore section with a contiguous portion of said flexible tube being located in said first bore section.

4. The external catheter of claim 3, wherein said distal end of said tubular coupler is spaced by a distance in the range of 1 inch to 2 inch from said apex, and wherein said cover includes a hollow cavity extending along said longitudinal central axis from said distal end of said tubular coupler to a point in the range of 0.125 inch to 1 inch from said apex.

* * * * *